(12) United States Patent
Ren

(10) Patent No.: US 8,927,687 B2
(45) Date of Patent: Jan. 6, 2015

(54) MICROCRYSTALLINE Y RECEPTOR AGONISTS

(75) Inventor: Steven Shijun Ren, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 0 days.

(21) Appl. No.: 13/809,136

(22) PCT Filed: Jul. 8, 2011

(86) PCT No.: PCT/US2011/043420
§ 371 (c)(1),
(2), (4) Date: May 1, 2013

(87) PCT Pub. No.: WO2012/006566
PCT Pub. Date: Jan. 12, 2012

(65) Prior Publication Data
US 2013/0296225 A1    Nov. 7, 2013

Related U.S. Application Data

(60) Provisional application No. 61/363,200, filed on Jul. 9, 2010.

(51) Int. Cl.
*C07K 2/00*    (2006.01)

(52) U.S. Cl.
USPC .............................................. 530/300; 514/1

(58) Field of Classification Search
USPC ...................... 536/23.1, 24.1; 530/300; 514/1
See application file for complete search history.

(56) References Cited

U.S. PATENT DOCUMENTS 5,273,960 A * 12/1993 Nyeki et al. ................ 514/21.9
6,380,357 B2   4/2002 Hermeling et al.
6,596,081 B1 * 7/2003 Arnowitz et al. ............ 117/201
7,001,892 B1   2/2006 Chmielewski et al.
2003/0044463 A1   3/2003 Deghenghi et al.
2003/0073134 A1 * 4/2003 Louie et al. .................... 435/7.1
2010/0099619 A1 * 4/2010 Levy et al. ...................... 514/12

FOREIGN PATENT DOCUMENTS

WO    WO 2005/077094    8/2005

OTHER PUBLICATIONS

Wood et al., "Purification Crystallization and Preliminary X-ray Studies on Avian Pancreatic Polypeptide", European Journal of Biochemistry, vol. 78, No. 1, (1977), p. 119-126.
Hoffman et al., Crystallization of Bovine Pancreatic Polypeptide, Biochemical and Biophysical Research Communications, vol. 116, No. 3, (1983), p. 830-835.
Cox et al., Neuropeptide Y, Y1, Y2 and Y4 receptors mediate Y agonist reponses in isolated human colon mucosa, British Journal of Pharmacology, vol. 135, No. 6, (2002), p. 1505-1512.
Unniappan et al., "Effects of dipeptidyl peptidase IV on the satiety actions of peptide YY", Diabetologia, vol. 49, No. 8, (2006), p. 1915-1923.
Supplementary European Search Report for European application No. 11804434 (Mar. 13, 2013).
Blundell et al., "X-ray analysis (1.4-A resolution) of avian pancreatic polypeptide: small globular protein hormone," PNAS 1981, 78(7): 4175-4179; (p. 4175, col. 2, para 3).
Wood et al., "Purification, crystallization and preliminary X-ray studies on avian pancreatic polypepide," Eur. J. Biochem. (1977) 78;119-126 (p. 122, col. 1, para 1).
International Search Report of PCT/US2011/043420 mailed Feb. 3, 2012.

* cited by examiner

*Primary Examiner* — Ardin Marschel
(74) *Attorney, Agent, or Firm* — Womble Carlyle Sandridge & Rice, LLP

(57) ABSTRACT

The disclosure provides microcrystals of Y receptor agonists; microcrystalline pellets of Y receptor agonists, and microcrystalline suspensions of Y receptor agonists. Pharmaceutical compositions containing these microcrystals, microcrystalline pellets, and microcrystalline suspensions have prolonged pharmacokinetic profiles making them useful for once daily or once weekly administration.

9 Claims, 7 Drawing Sheets

MICROCRYSTALLINE Y RECEPTOR AGONISTS

RELATED APPLICATIONS

This application is a Section 371 of PCT/US2011/043420 filed Jul. 8, 2011, which claims priority to U.S. Application No. 61/363,200 filed Jul. 9, 2010 the disclosure of which is incorporated herein.

FIELD

The disclosure provides compounds, compositions and pharmaceutical formulations of microcrystalline Y receptor agonists.

SEQUENCE LISTING

A computer-readable copy of a sequence listing in text format (.txt) is submitted as part of the specification.

BACKGROUND

Protein crystals have shown significant benefits in the delivery of bioactives to achieve high concentration, low viscosity, extended release profiles, and improved stability. Li et al, Acta Cryst., F63:599-601 (2007); Basu et al, Expert Opin. Biol. Ther., 4(3):301-317 (2004); Yang et al, PNAS, 100(12): 6934-6939 (2003). Some proteins and peptides have been crystallized alone or co-crystallized with zinc in an attempt to make extended release products. Y receptor agonists, complex compounds that often possess inadequate stability and short half-life, have limited delivery options. There is a need in the art for formulations of Y receptor agonists that have extended release properties and that have suitable stability. The disclosure is directed to these, as well as other, important ends.

SUMMARY

The disclosure is based on the unexpected discovered that microcrystals of Y receptor agonists may be produced that have extended pharmacokinetic profiles. Therefore, pharmaceutical compositions containing the Y receptor agonists may be administered to the patient once per day, once every other day, or once per week.

The disclosure provides microcrystals of Y receptor agonists, wherein the microcrystals have a particle size from about 1 micron to about 25 microns and are birefringent under a polarized light microscope. In one embodiment, the microcrystals are complexed with metals. In one embodiment, the microcrystals are coated with polyamino. In one embodiment, the microcrystals are complexed with metals and coated with polyamino acids.

The disclosure provides methods for preparing compositions comprising microcrystals of Y receptor agonists by (i) dissolving a Y receptor agonist peptide in an aqueous solution at a pH of about 3 to about 5, wherein the aqueous solution optionally contains a dissolution agent to facilitate dissolution of the Y receptor agonist, to produce a first aqueous solution having the Y receptor agonist peptide dissolved therein; (ii) adjusting the pH of the first aqueous solution upward to a pH of about 4.0 to about 7.5, to produce a second aqueous solution having the Y receptor agonist peptide dissolved therein; and (iii) stirring the second aqueous solution at a temperature from about 1° C. to about 10° C. for more than one day; thereby producing the composition. The compositions may be referred to as microcrystalline suspensions. Following the additional step of drying, the compositions may be referred to as microcrystalline pellets. In one embodiment, the methods may further comprise the addition of metals to form metal complexes of the microcrystals. In one embodiment, the methods may further comprise the addition of polyamino acids to form microcrystals coated with polyamino acids. In one embodiment, the methods may further comprise the addition of metals and polyamino acids to form metal-complexed microcrystals coated with polyamino acids.

DETAILED DESCRIPTION

The disclosure is based on the surprising and advantageous benefits of microcrystals of Y receptor agonist peptides. It has been discovered that microcrystals of Y receptor agonist peptides have improvements with regard to, e.g., increased efficacy, extended pharmacokinetic profile and bioavailability (e.g., allowing for once daily or once weekly administration), and increased stability, relative to that observed with noncrystalline solutions of Y receptor agonist peptides. This results in improved efficacy with regard to, e.g., patient compliance, reductions in body weight, weight loss, reduction in food intake, and beneficial alteration in body composition (e.g., fat-specific weight loss, and/or lean-sparing weight loss), relative to the efficacy observed with noncrystalline solutions of such Y receptor agonists.

Figure 1:
FIG. 1 is a microscopic picture of microcrystals of the Y receptor agonist peptide having SEQ ID NO:438.
Figure 2:
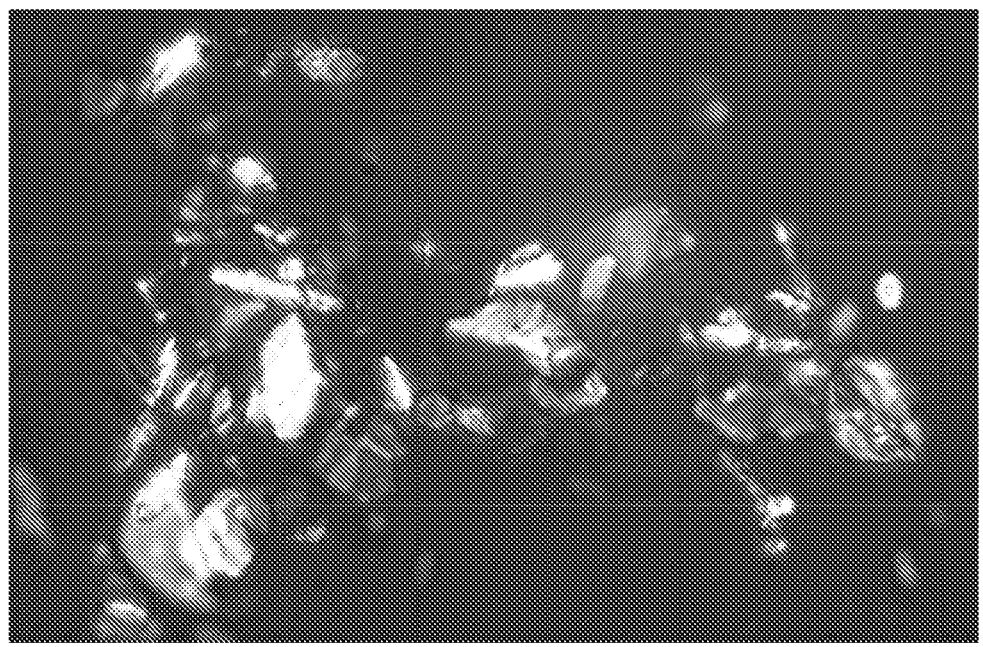
FIG. 2 is a polarized light microscopic picture showing that the microcrystals of the Y receptor agonist peptide having SEQ ID NO:438 exhibit birefringence.
Figure 3:
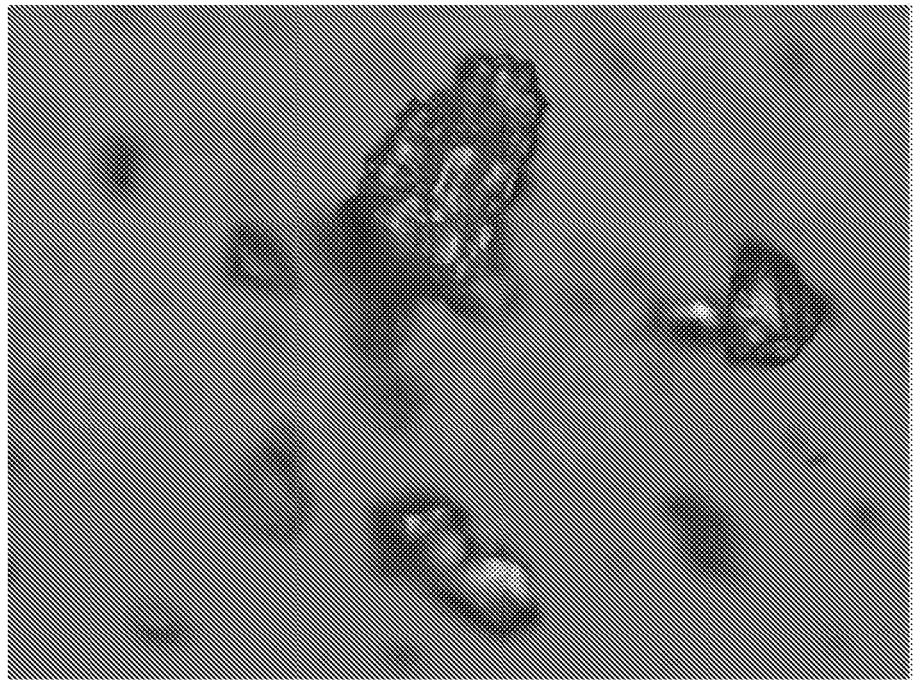
FIG. 3 is a microscopic picture of microcrystals of the Y receptor agonist peptide having SEQ ID NO:281.
Figure 4:
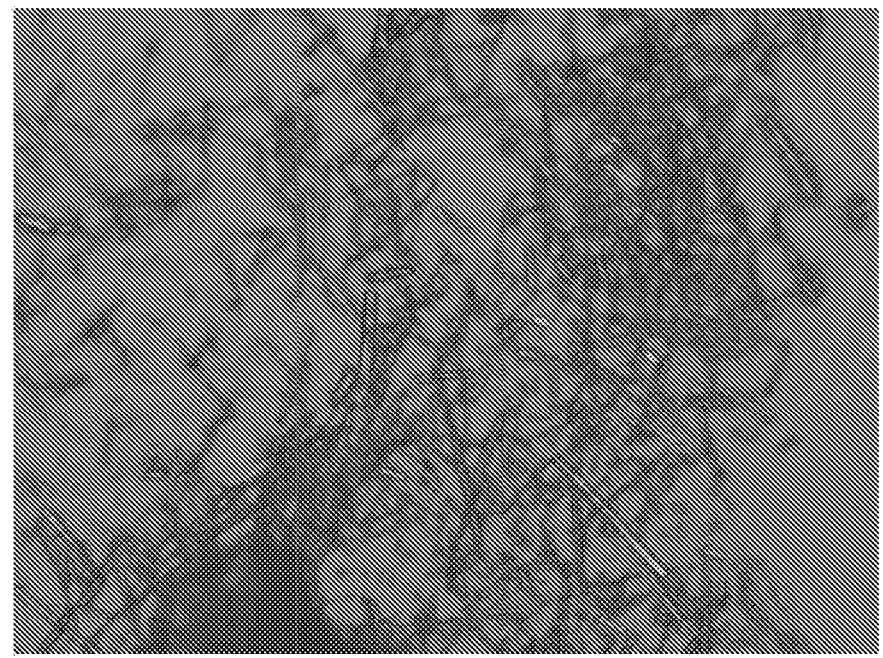
FIG. 4 is a microscopic picture of microcrystals of the Y receptor agonist peptide having SEQ ID NO:439.

The term "microcrystals" refers to Y receptor agonist peptides having a particle size ranging from about 1 micron to about 25 microns. In one embodiment, "microcrystals" refers to Y receptor agonist peptides having a particle size ranging from about 1 micron to about 25 microns, where the microcrystals are birefringent (i.e., have two indices of refraction) under polarized light. In one embodiment, "microcrystals" refers to Y receptor agonist peptides having a particle size ranging from about 1 micron to about 25 microns, where the microcrystals are birefringent (i.e., have two indices of refraction) under polarized light, and where the microcrystals have an alpha-helical structure, a beta-sheet secondary structure, or an alpha-helical structure and a beta-sheet secondary structure when viewed by infrared spectroscopy (e.g., using an FTIR spectrometer). In one embodiment, the microcrystals have a particle size ranging from about 1 micron to about 15 microns. In one embodiment, the microcrystals have a particle size ranging from about 1 micron to about 10 microns. In one embodiment, the microcrystals have a particle size ranging from about 5 microns to about 15 microns. In one embodiment, the microcrystals have a particle size ranging from about 5 microns to about 10 microns. In another embodiment, the microcrystals have (i) oval-shaped crystals; (ii) blade-like crystals; or (iii) oval-shaped crystals and blade-like crystals. Microcrystals are shown in FIGS. 1-5. FIG. 2 shows that the microcrystals are birefringent when viewed under a polarized light microscope. Microcrystals having an oval shape are shown in FIGS. 1 and 3. Microcrystals having a thin blade shape or a blade-like shape are shown in FIG. 4.

Figure 5:
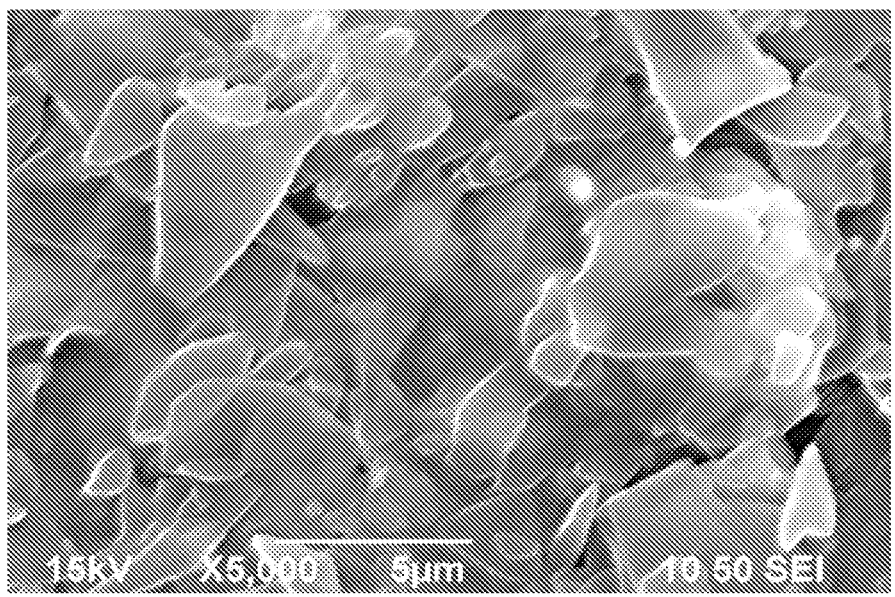
FIG. 5 is a microscopic picture of microcrystalline pellets of the Y receptor agonist peptide having SEQ ID NO:438.

The term "microcrystalline pellets" refers to a plurality of microcrystals. Microcrystalline pellets are shown in FIG. 5 (viewed under a microscopic).

The term "microcrystalline suspension" refers to a plurality of microcrystals dispersed or suspended in an aqueous solution. In one embodiment, the term "microcrystalline suspension" refers to microcrystalline pellets that are dispersed or suspended in an aqueous solution.

The term "aqueous solution" is a solution in which the solvent is water. The aqueous solutions described herein may further comprise pharmaceutically acceptable excipients, as described herein.

The microcrystals are prepared by dissolving one or more Y receptor agonist peptides in an aqueous solution having a pH from about 3 to about 5 to produce a first aqueous solution having the Y receptor agonist dissolved therein. The pH of the solution may be adjusted to a pH from about 3 to about 5 using any buffer known in the art. Exemplary buffers include phosphate buffers, acetate buffers, citrate buffers, glutamate buffers, and the like. In one embodiment, the buffer is a phosphate buffer. In one embodiment, the pH of the first aqueous solution is from about 3.5 to about 4.5.

In one embodiment, the aqueous solution further comprises a dissolution agent to facilitate or enhance dissolution of the Y receptor agonist. Any dissolution agent known in the art may be used. In one embodiment, the dissolution agent is a polyol. Exemplary polyols include glycerol, mannitol, sorbitol, sucrose, glycol, ethylene glycol, pentaerythritol, and the like. In one embodiment, the polyol is glycerol. The amount of dissolution agent used will vary with the particular requirements of any Y receptor agonist.

After the Y receptor agonist is dissolved in the first aqueous solution, then the pH of the first aqueous solution is adjusted upward to a pH of about 4 to about 7.5 to produce a second aqueous solution having the Y receptor agonist dissolved therein. The pH can be adjusted upward using any buffer known in the art. Exemplary buffers include phosphate buffers, Tris buffers, citrate buffers, glutamate buffers, and the like. In one embodiment, the buffer is a phosphate buffer. In one embodiment, the pH of the second aqueous solution is from about 4 to about 5.5. In one embodiment, the pH of the second aqueous solution is from about 5.5 to about 7.5.

Thereafter, microcrystals are formed by stirring the second aqueous solution at a temperature of about 1° C. to about 10° C. for at least one hour. The microcrystals begin to form during this process, until a plurality of microcrystals develop (substantially maintaining their crystal structure) to form a microcrystalline suspension. In one embodiment, the second aqueous solution is stirred at a temperature from about 1° C. to about 8° C. In one embodiment, the second aqueous solution is stirred at a temperature from about 3° C. to about 6° C. In one embodiment, the second aqueous solution is stirred for at least 12 hours. In one embodiment, the second aqueous solution is stirred for at least one day. In one embodiment, the second aqueous solution is stirred from about one day to about one month. In one embodiment, the second aqueous solution is stirred from about one day to about ten days.

The microcrystalline suspension can be dried to produce microcrystalline pellets.

The final concentration of peptide in the microcrystalline suspension may be from 0.2 mg/mL to 10 mg/mL. The final concentration of peptide in the microcrystalline may be determined by the pH of the second aqueous solution. Generally, when the pH of the second aqueous solution is from 4 to 5.5, the concentration of peptide in the microcrystalline suspension is from 5 mg/mL to 10 mg/mL. Generally, when the pH of the second aqueous solution is from 5.5 to 7.5, the concentration of peptide in the microcrystalline suspension is from 0.2 mg/mL to 5 mg/mL.

As described in the Examples below, the individual microcrystals have structures exemplified in FIG. 1 (viewed under a microscope) and FIG. 2 (exhibiting birefringence when viewed under a polarized light microscope). Upon drying the microcrystalline suspension, the resulting microcrystalline pellets (e.g., plurality or group of microcrystals) have the structures exemplified in FIG. 3.

Pharmaceutical compositions can be prepared using the microcrystalline suspension and/or the microcrystalline pellets. Other pharmaceutically acceptable excipients known in the art and described herein may be added to the pharmaceutical compositions to exhibit the desired pharmaceutical properties.

In another embodiment, the disclosure provides microcrystals of Y receptor agonists coated with polyamino acids. The polyamino acids may be any known in the art. The polyamino acids may be in the form of poly-L-amino acids. Exemplary poly-amino acids include poly-glutamic acid (poly-L-glutamic acid), poly-lysine (poly-L-lysine), poly-arginine (poly-L-arginine), poly-aspartic acid (poly-L-aspartic acid), poly-ornithine (poly-L-ornithine), and the like. In one embodiment, the poly-amino acid is poly-L-glutamic acid. In one embodiment, the microcrystals are coated with two different polyamino acids. The microcrystals can be partially coated, substantially coated, or completely coated with the polyamino acids, depending on the amount of polyamino acid used in the preparation. Similarly, the polyamino acid coating can be any thickness, depending on the amount of polyamino acid used in the preparation. Following the methods described herein, the skilled artisan can vary and optimize the amount of polyamino acid used in the process for coating the microcrystals.

The microcrystals are prepared by dissolving one or more Y receptor agonist peptides in an aqueous solution having a pH from about 3 to about 5 to produce a first aqueous solution having the Y receptor agonist dissolved therein. The pH of the solution may be adjusted using any buffer known in the art. Exemplary buffers include phosphate buffers, acetate buffers, citrate buffers, glutamate buffers, and the like. In one embodiment, the buffer is a phosphate buffer. In one embodiment, the pH of the first aqueous solution is from about 3.5 to about 4.5. In one embodiment, the aqueous solution further comprises a dissolution agent to facilitate or enhance dissolution of the Y receptor agonist. Any dissolution agent known in the art may be used. In one embodiment, the dissolution agent is a polyol. Exemplary polyols include glycerol, mannitol, sorbitol, sucrose, glycol, ethylene glycol, pentaerythritol, and the like. In one embodiment, the polyol is glycerol.

After the Y receptor agonist is dissolved in the first aqueous solution, then the pH of the first aqueous solution is adjusted upward to a pH of about 4 to about 7.5 to produce a second aqueous solution. The pH can be adjusted upward using any buffer known in the art. Exemplary buffers include phosphate buffers, Tris buffers, citrate buffers, glutamate buffers, and the like. In one embodiment, the buffer is a phosphate buffer. In one embodiment, the pH of the second aqueous solution is from about 4 to about 5.5. In one embodiment, the pH of the second aqueous solution is from about 5.5 to about 7.5.

Thereafter, microcrystals are formed by stirring the second aqueous solution at a temperature of about 1° C. to about 10° C. for at least one hour. The microcrystals begin to form during this process, until a plurality of microcrystals develop (substantially maintaining their crystal structure) to form a microcrystalline suspension. In one embodiment, the second aqueous solution is stirred at a temperature from about 1° C. to about 8° C. In one embodiment, the second aqueous solution is stirred at a temperature from about 3° C. to about 6° C. In one embodiment, the second aqueous solution is stirred for at least 12 hours. In one embodiment, the second aqueous solution is stirred for at least one day. In one embodiment, the second aqueous solution is stirred from about one day to about one month. In one embodiment, the second aqueous solution is stirred from about one day to about ten days.

During or after formation of the microcrystalline suspension, one or more polyamino acids are added to the microcrystalline suspension at the pH of the microcrystalline suspension and the microcrystalline suspension and the polyamino acids are stirred at a temperature of about 1° C. to about 10° C. for at least one hour. The polyamino acids may be in the form of an aqueous solution at a pH substantially the same as the pH of the microcrystalline suspension. In one embodiment, the polyamino acids are added after formation of the microcrystalline suspension. In one embodiment, the microcrystalline suspension and the polyamino acids are stirred at a temperature from about 1° C. to about 8° C. In one embodiment, the microcrystalline suspension and the polyamino acids are stirred at a temperature from about 3° C. to about 6° C. In one embodiment, the microcrystalline suspension and the polyamino acids are stirred for at least 12 hours. In one embodiment, the microcrystalline suspension and the polyamino acids are stirred for at least one day. In one embodiment, the microcrystalline suspension and the polyamino acids are stirred from about one day to about one month. In one embodiment, the microcrystalline suspension and the polyamino acids are stirred from about one day to about ten days. This results in a microcrystalline suspension where the microcrystals are coated with the polyamino acid. The microcrystalline suspension can then be dried to produce microcrystalline pellets where the microcrystals are coated with the polyamino acid.

The final concentration of peptide in the microcrystalline suspension may be from 0.2 mg/mL to 10 mg/mL. The final concentration of peptide in the microcrystalline may be determined by the pH of the second aqueous solution. Generally, when the pH of the second aqueous solution is from 4 to 5.5, the concentration of peptide in the microcrystalline suspension is from 5 mg/mL to 10 mg/mL. Generally, when the pH of the second aqueous solution is from 5.5 to 7.5, the concentration of peptide in the microcrystalline suspension is from 0.2 mg/mL to 5 mg/mL.

In the methods described herein, the skilled artisan will be able to use an amount of polyamino acid to achieve a weight ratio of peptide:polyamino acid in the range of 1:1 to 10:1. In one embodiment, the weight ratio of peptide:polyamino acid may be in the range of 2:1 to 6:1. In one embodiment, the weight ratio of peptide:polyamino acid may be in the range of 4:1 to 6:1.

Pharmaceutical compositions can be prepared using the polyamino acid-coated microcrystalline suspension and/or the polyamino acid-coated microcrystalline pellets. Other pharmaceutically acceptable excipients may be added to the pharmaceutical compositions to exhibit the desired pharmaceutical properties. In one embodiment, the pharmaceutically acceptable excipient is a preservative, such as meta-cresol.

The disclosure provides microcrystals complexed with one or more metals. The metals are generally in the form of salts. The metals are preferably alkaline earth metals, transition metals or a combination thereof. Exemplary transition metals include zinc, iron, nickel, copper, and the like. Exemplary alkaline earth metals include calcium, magnesium, and the like. In one embodiment, the microcrystals are complexed with zinc, magnesium, calcium, or a combination of two or more thereof. In one embodiment, the microcrystals are complexed with zinc.

The microcrystals are prepared by dissolving one or more Y receptor agonist peptides in an aqueous solution having a pH from about 3 to about 5 to produce a first aqueous solution having the Y receptor agonist dissolved therein. The pH of the solution may be adjusted using any buffer known in the art. Exemplary buffers include phosphate buffers, acetate buffers, citrate buffers, glutamate buffers, and the like. In one embodiment, the buffer is a phosphate buffer. In one embodiment, the pH of the first aqueous solution is from about 3.5 to about 4.5. In one embodiment, the aqueous solution further comprises a dissolution agent to facilitate or enhance dissolution of the Y receptor agonist. Any dissolution agent known in the art may be used. In one embodiment, the dissolution agent is a polyol. Exemplary polyols include glycerol, mannitol, sorbitol, sucrose, glycol, ethylene glycol, pentaerythritol, and the like. In one embodiment, the polyol is glycerol.

Thereafter, one or more metals, preferably in the form of the metal salt, are added to the first aqueous solution. Then the pH of the first aqueous solution is adjusted upward to a pH of about 4 to about 7.5 to produce a second aqueous solution. The pH can be adjusted using any buffer known in the art. Exemplary buffers include phosphate buffers, Tris buffers, citrate buffers, glutamate buffers, and the like. In one embodiment, the buffer is a phosphate buffer. In one embodiment, the pH of the second aqueous solution is from about 4 to about 5.5. In one embodiment, the pH of the second aqueous solution is from about 5.5 to about 7.5.

Thereafter, microcrystals complexed with the metals are formed by stirring the second aqueous solution at a temperature of about 1° C. to about 10° C. for at least one hour. The metal-complexed microcrystals begin to form during this process, until a plurality of metal-complexed microcrystals develop (substantially maintaining their crystal structure) to form a metal-complexed microcrystalline suspension. In one embodiment, the second aqueous solution is stirred at a temperature from about 1° C. to about 8° C. In one embodiment, the second aqueous solution is stirred at a temperature from about 3° C. to about 6° C. In one embodiment, the second aqueous solution is stirred for at least 12 hours. In one embodiment, the second aqueous solution is stirred for at least one day. In one embodiment, the second aqueous solution is stirred from about one day to about one month. In one embodiment, the second aqueous solution is stirred from about one day to about ten days.

The final concentration of peptide in the microcrystalline suspension may be from 0.2 mg/mL to 10 mg/mL. The final concentration of peptide in the microcrystalline may be determined by the pH of the second aqueous solution. Generally, when the pH of the second aqueous solution is from 4 to 5.5, the concentration of peptide in the microcrystalline suspension is from 5 mg/mL to 10 mg/mL. Generally, when the pH of the second aqueous solution is from 5.5 to 7.5, the concentration of peptide in the microcrystalline suspension is from 0.2 mg/mL to 5 mg/mL.

Based on the methods described herein, the skilled artisan will be able to use an amount of metal to achieve a weight ratio of peptide:metal of 1:1 to 10:1. In one embodiment, the weight ratio of peptide:metal is 1:1 to 5:1. In one embodiment, the weight ratio of peptide:metal is 1:1 to 4:1. In one embodiment, the weight ratio of peptide:metal is 1:1 to 3:1. In one embodiment, the weight ratio of peptide:metal is 1:1 to 2:1. In one embodiment, the weight ratio of peptide:metal is 3:1. In one embodiment, the weight ratio of peptide:metal is 2:1. In one embodiment, the weight ratio of peptide:metal is 1:1.

Pharmaceutical compositions can be prepared using the metal-complexed microcrystalline suspension and/or the metal-complexed microcrystalline pellets. Other pharmaceutically acceptable excipients may be added to the pharmaceutical compositions to exhibit the desired pharmaceutical properties. In one embodiment, the pharmaceutically acceptable excipient is a preservative, such as meta-cresol.

The disclosure provides microcrystals complexed with one or more metals and coated with polyamino acids. The metals are generally in the form of salts. The metals are preferably alkaline earth metals, transition metals or a combination thereof. Exemplary transition metals include zinc, iron, nickel, copper, and the like. Exemplary alkaline earth metals include calcium, magnesium, and the like. In one embodiment, the microcrystals are complexed with zinc, magnesium, calcium, or a combination of two or more thereof. In one embodiment, the microcrystals are complexed with zinc. The polyamino acids may be any known in the art. The polyamino acids may be in the form of poly-L-amino acids. Exemplary poly-amino acids include poly-glutamic acid (poly-L-glutamic acid), poly-lysine (poly-L-lysine), poly-arginine (poly-L-arginine), poly-aspartic acid (poly-L-aspartic acid), poly-ornithine (poly-L-ornithine), and the like. In one embodiment, the poly-amino acid is poly-L-glutamic acid. In one embodiment, the microcrystals are coated with two different polyamino acids. The microcrystals can be partially coated, substantially coated, or completely coated with the polyamino acids, depending on the amount of polyamino acid used in the preparation. Similarly, the polyamino acid coating can be any thickness, depending on the amount of polyamino acid used in the preparation. Following the methods described herein, the skilled artisan can vary and optimize the amount of polyamino acid used in the process for coating the microcrystals.

The microcrystals are prepared by dissolving one or more Y receptor agonist peptides in an aqueous solution having a pH from about 3 to about 5 to produce a first aqueous solution having the Y receptor agonist dissolved therein. The pH of the solution may be adjusted using any buffer known in the art. Exemplary buffers include phosphate buffers, acetate buffers, citrate buffers, glutamate buffers, and the like. In one embodiment, the buffer is a phosphate buffer. In one embodiment, the pH of the first aqueous solution is from about 3.5 to about 4.5. In one embodiment, the aqueous solution further comprises a dissolution agent to facilitate or enhance dissolution of the Y receptor agonist. Any dissolution agent known in the art may be used. In one embodiment, the dissolution agent is a polyol. Exemplary polyols include glycerol, mannitol, sorbitol, sucrose, glycol, ethylene glycol, pentaerythritol, and the like. In one embodiment, the polyol is glycerol.

Thereafter, one or more metals, preferably in the form of the metal salt, are added to the first aqueous solution. Then the pH of the first aqueous solution is adjusted upward to a pH of about 4 to about 7.5 to produce a second aqueous solution. The pH can be adjusted using any buffer known in the art. Exemplary buffers include phosphate buffers, Tris buffers, citrate buffers, glutamate buffers, and the like. In one embodiment, the buffer is a phosphate buffer. In one embodiment, the pH of the second aqueous solution is from about 4 to about 5.5. In one embodiment, the pH of the second aqueous solution is from about 5.5 to about 7.5.

Thereafter, microcrystals complexed with the metals are formed by stirring the second aqueous solution at a temperature of about 1° C. to about 10° C. for at least one hour. The metal-complexed microcrystals begin to form during this process, until a plurality of metal-complexed microcrystals develop (substantially maintaining their crystal structure) to form a metal-complexed microcrystalline suspension. In one embodiment, the second aqueous solution is stirred at a temperature from about 1° C. to about 8° C. In one embodiment, the second aqueous solution is stirred at a temperature from about 3° C. to about 6° C. In one embodiment, the second aqueous solution is stirred for at least 12 hours. In one embodiment, the second aqueous solution is stirred for at least one day. In one embodiment, the second aqueous solution is stirred from about one day to about one month. In one embodiment, the second aqueous solution is stirred from about one day to about ten days.

During or after formation of the metal-complexed microcrystalline suspension, one or more polyamino acids are added to the metal-complexed microcrystalline suspension at the pH of the metal-complexed microcrystalline suspension and the metal-complexed microcrystalline suspension and the polyamino acids are stirred at a temperature of about 1° C. to about 10° C. for at least one hour. The polyamino acids may be in the form of an aqueous solution at a pH substantially the same as the pH of the metal-complexed microcrystalline suspension. In one embodiment, the polyamino acids are added after formation of the metal-complexed microcrystalline suspension. In one embodiment, the metal-complexed microcrystalline suspension and the polyamino acids are stirred at a temperature from about 1° C. to about 8° C. In one embodiment, the metal-complexed microcrystalline suspension and the polyamino acids are stirred at a temperature from about 3° C. to about 6° C. In one embodiment, the metal-complexed microcrystalline suspension and the polyamino acids are stirred for at least 12 hours. In one embodiment, the metal-complexed microcrystalline suspension and the polyamino acids are stirred for at least one day. In one embodiment, the metal-complexed microcrystalline suspension and the polyamino acids are stirred from about one day to about one month. In one embodiment, the metal-complexed microcrystalline suspension and the polyamino acids are stirred from about one day to about ten days. This results in a metal-complexed microcrystalline suspension where the metal-complexed microcrystals are coated with the polyamino acid. The polyamino acid-coated, metal-complexed microcrystalline suspension can then be dried to produce microcrystalline pellets where the microcrystals are complexed with metals and coated with the polyamino acid.

The final concentration of peptide in the microcrystalline suspension may be from 0.2 mg/mL to 10 mg/mL. The final concentration of peptide in the microcrystalline may be determined by the pH of the second aqueous solution. Generally, when the pH of the second aqueous solution is from 4 to 5.5, the concentration of peptide in the microcrystalline suspension is from 5 mg/mL to 10 mg/mL. Generally, when the pH of the second aqueous solution is from 5.5 to 7.5, the concentration of peptide in the microcrystalline suspension is from 0.2 mg/mL to 5 mg/mL. In the methods described herein, the skilled artisan will be able to use an amount of polyamino acid to achieve a weight ratio of peptide:polyamino acid in the range of 1:1 to 10:1. In one embodiment, the weight ratio of peptide:polyamino acid may be in the range of 2:1 to 6:1. In one embodiment, the weight ratio of peptide:polyamino acid may be in the range of 4:1 to 6:1. Based on the methods described herein, the skilled artisan will be able to use an amount of metal to achieve a weight ratio of peptide:metal of 1:1 to 10:1. In one embodiment, the weight ratio of peptide:metal is 1:1 to 5:1. In one embodiment, the weight ratio of peptide:metal is 1:1 to 4:1. In one embodiment, the weight ratio of peptide:metal is 1:1 to 3:1. In one embodiment, the weight ratio of peptide:metal is 1:1 to 2:1. In one embodiment, the weight ratio of peptide:metal is 3:1. In one embodiment, the weight ratio of peptide:metal is 2:1. In one embodiment, the weight ratio of peptide:metal is 1:1.

Pharmaceutical compositions can be prepared using the polyamino acid-coated, metal-complexed microcrystalline suspension and/or the polyamino acid-coated, metal-complexed microcrystalline pellets. Other pharmaceutically acceptable excipients may be added to the pharmaceutical compositions to exhibit the desired pharmaceutical properties. In one embodiment, the pharmaceutically acceptable excipient is a preservative, such as meta-cresol.

Any Y receptor agonist peptide known in the art may be used to form the microcrystals described herein. Exemplary Y receptor agonist peptides are described in, e.g., U.S. Pat. No. 7,723,471; US Publication No. 2006/0094653; US Publication No. 2010/0099619; PCT Publication No. WO 2009/138511; PCT Publication No. WO 2011/033068; or PCT Publication No. WO 2011/058165, the disclosures of which are incorporated by reference herein.

In one embodiment, the Y receptor agonist peptide is PYY(3-36) (SEQ ID NO:3). In one embodiment, the Y receptor agonist is a PYY analog.

"PYY analog" refers to a peptide that has at least 70%, at least 80%, at least 85%, at least 90%o, at least 94%, or at least 97% sequence identity to PYY(3-36) over the entire length of PYY(3-36). In one embodiment, the PYY analog has at least 80% sequence identity to PYY(3-36) over the entire length of PYY(3-36). In one embodiment, the PYY analog has at least 85% sequence identity to PYY(3-36) over the entire length of PYY(3-36). In one embodiment, the PYY analog has at least 90% sequence identity to PYY(3-36) over the entire length of PYY(3-36). In one embodiment, the PYY analog has at least 94% sequence identity to PYY(3-36) over the entire length of PYY(3-36). In one embodiment, the PYY analog has at least 97% sequence identity to PYY(3-36) over the entire length of PYY(3-36).

In one embodiment, the PYY analog may be a chimeric peptide. In this emobodiment, PYY(3-36) (SEQ ID NO:3) may comprise amino acid sequences from the pancreatic polypeptide ("PP") (SEQ ID NO: 1) and/or neuropeptide Y (SEQ ID NO:4) in order to vary the properties of the peptide.

In other embodiments, the PYY analogs may be from 30 to 36 amino acids in length; preferably from 32 to 34 amino acids in length. The skilled artisan will appreciate that PYY analogs may be prepared by the addition of amino acids to the amino acid sequence of PYY(3-36) (e.g., at the C-terminus, N-terminus, within the peptide, or a combination thereof); the deletion of amino acids from the amino acid sequence of PYY(3-36) (e.g., at the C-terminus, N-terminus, within the peptide, or a combination thereof); substitutions of any of the amino acids for different amino acids in the amino acid sequence in PYY(3-6); or a combination of two or more of additions, deletions, and substitutions. As used herein, the term "substitution" includes modifications made to an amino acid (e.g., an amino acid is substituted with a modified version of the original amino acid). Typical modifications to amino acids include amides, carbohydrates, alkyl groups, acyl groups, fatty acyl groups, esters, and the like.

Exemplary Y receptor agonists are set forth in the Sequence Listing submitted herewith as part of the specification and incorporated by reference herein. Such Exemplary Y receptor agonists include SEQ ID NOs: 1-483. These Y receptor agonist peptides are also described in U.S. Pat. No. 7,723,471.

In one embodiment the PYY analog has the amino acid sequence of SEQ ID NO:483:

$Xaa_1$ Lys Pro Glu $Xaa_5$ Pro Gly Glu Asp Ala Ser Pro $Xaa_{13}$ Glu Glu Leu Ala Arg

Tyr Tyr $Xaa_{21}$ $Xaa_{22}$ Leu Arg $Xaa_{25}$ Tyr Ile Asn Leu Ile Thr Arg Gin Arg $Xaa_{35}$, wherein $Xaa_1$ is Ile, isocaproyl-Ile, Pro, or isocaproyl-Pro; $Xaa_5$ is His or Ala; $Xaa_{13}$ is Ala or absent; $Xaa_{21}$ is Ala or Ser; $Xaa_{22}$ is Ser or Ala; $Xaa_{25}$ is Ala or His; and $Xaa_{35}$ is Tyr-OH or Tyr-$NH_2$.

In one embodiment, the peptide of SEQ ID NO:483 is SEQ ID NO:438: Pro Lys Pro Glu His Pro Gly Glu Asp Ala Ser Pro Glu Glu Leu Ala Arg Tyr Tyr Ala Ser Leu Arg Ala Tyr Ile Asn Leu Ile Thr Arg Gin Arg Tyr (SEQ ID NO:438).

In one embodiment, the peptide of SEQ ID NO:483 is SEQ ID NO:281: isocaproyl-Ile Lys Pro Glu Ala Pro Gly Glu Asp Ala Ser Pro Glu Glu Leu Ala Arg Tyr Tyr Ser Ala Leu Arg His Tyr Ile Asn Leu Ile Thr Arg Gin Arg Tyr (SEQ ID NO:281).

In one embodiment, the peptide of SEQ ID NO:483 is SEQ ID NO:439: Pro Lys Pro Glu His Pro Gly Glu Asp Ala Ser Ala Glu Glu Leu Ala Arg Tyr Tyr Ala Ser Leu Arg Ala Tyr Ile Asn Leu Ile Thr Arg Gin Arg Tyr (SEQ ID NO:439).

In one embodiment, the Y Receptor agonist comprises the amino acid sequence of SEQ ID NO:30. In one embodiment, the Y Receptor agonist comprises the amino acid sequence of SEQ ID NO:88. In one embodiment, the Y Receptor agonist comprises the amino acid sequence of SEQ ID NO:348. In one embodiment, the Y Receptor agonist comprises the amino acid sequence of SEQ ID NO:349. In one embodiment, the Y Receptor agonist comprises the amino acid sequence of SEQ ID NO:350. In one embodiment, the Y Receptor agonist comprises the amino acid sequence of SEQ ID NO:481. In one embodiment, the Y Receptor agonist comprises the amino acid sequence of SEQ ID NO:482.

In one embodiment, the Y receptor agonist is a PYY analog that has at least 70% sequence identity to PYY(3-36) over the entire length of PYY(3-36). In one embodiment, the Y receptor agonist is a PYY analog that has at least 80% sequence identity to PYY(3-36) over the entire length of PYY(3-36). In one embodiment, the Y receptor agonist is a PYY analog that has at least 85% sequence identity to PYY(3-36) over the entire length of PYY(3-36). In one embodiment, the Y receptor agonist is a PYY analog that has at least 90% sequence identity to PYY(3-36) over the entire length of PYY(3-36). In one embodiment, the Y receptor agonist is a PYY analog that has at least 94% sequence identity to PYY(3-36) over the entire length of PYY(3-36). In one embodiment, the Y receptor agonist is a PYY analog that has at least 97% sequence identity to PYY(3-36) over the entire length of PYY(3-36).

In one embodiment, the Y receptor agonist is a compound described in PCT Publication No. WO 2009/138511. In one embodiment, the Y receptor agonist is a compound described in PCT Publication No. WO 2011/033068. In one embodiment, the Y receptor agonist is a compound described in WO 2011/058165

The Y receptor agonist peptides described herein may be formulated as pharmaceutically acceptable salts (e.g., acid addition salts) and/or complexes thereof. Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compositions and pharmaceutical compositions described herein may be provided in any form suitable for administration to a patient. In one embodiment, the pharmaceutical compositions are in a form suitable for oral administration. In one embodiment, the pharmaceutical compositions are in a form suitable for parenteral administration. Exemplary forms of parenteral administration include infusion, intravenous, intramuscular, subcutaneous, and the like. In one embodiment, the compositions and pharmaceutical formulations are provided in a form suitable for subcutaneous injection. The compositions and pharmaceutical compositions may be formulated with known pharmaceutically acceptable excipients, e.g., Remington's Pharmaceutical Sciences by E. W. Martin, including an aqueous solution.

Exemplary pharmaceutically acceptable excipients include buffers, isotonicity agents, preservatives, emulsifying agents, surfactants, chelating-agents, dissolution enhancing agents, and the like. Buffers include, for example, citrate buffers, acetate buffers, phosphate buffers, glutamate buffers, and the like. Isotonicity agents include, for example, sodium chloride, dextrose, boric acid, sodium tartrate, propylene glycol, polyols, or other inorganic or organic solutes. Emulsifying agents include, for example, acacia powder, a non-ionic surfactant, or an ionic surfactant). Preservatives include, for example, meta-cresol, sodium benzoate, potassium sorbate, phenol, methyl-paraben, ethyl-paraben, propyl-paraben, butyl-paraben, and the like. Other pharmaceutically acceptable excipients include, for example, calcium carbonate, calcium phosphate, sugars (e.g., lactose, glucose, sucrose), starch, cellulose derivatives, gelatin, vegetable oils, polyethylene glycol, and the like. The skilled artisan will appreciate that pharmaceutical compositions may contain one more excipients necessary to achieve the desired properties.

The pharmaceutical compositions described herein comprise the Y receptor agonist in therapeutically effective amounts. Typically, therapeutically effective amounts will be in the range of about 0.1 µg to about 10 mg/day; about 1 µg to about 5 mg/day; about 100 µg to about 1 mg/day; or about 5 µg to about 500 µg/day. The exact dose to be administered may be determined by one of skill in the art and is dependent upon the potency of the particular compound, as well as upon the age, weight and condition of the individual.

It was unexpectedly discovered that the microcrystals of Y receptor agonists have extended pharmacokinetic (pK) profiles. Therefore, the pharmaceutical compositions containing the Y receptor agonists may be administered to the patient once per day, once every other day, or once per week.

The compounds, compositions, and pharmaceutical compositions described herein may be used to treat any disease known in the art for which therapy with Y receptor agonists is appropriate. Exemplary diseases that may be treated using the compounds, compositions, and pharmaceutical compositions described herein include diabetes (e.g., type 1 diabetes, type 2 diabetes, gestational diabetes, pre-diabetes); obesity; overweight; fatty liver diseases (e.g., non-alcoholic steatohepatitis (NASH), nonalcoholic fatty liver disease (NAFLD)); gastrointestinal diseases (e.g., ulcerative colitis, diarrhea, short bowel syndrome, small intestinal bacterial overgrowth, irritable bowel syndrome, Crohn's disease); gallbladder disease, hypertension, dyslipidemia, cardiovascular disease, myocardial infarction, atherosclerosis, eating disorders, insulin-resistance, and the like. In one embodiment, the compounds, compositions, and pharmaceutical compositions described herein are used to treat diabetes (e.g., type 1 diabetes, type 2 diabetes, gestational diabetes, pre-diabetes) in a patient. The diabetes is preferably type 2 diabetes. In one embodiment, the compounds, compositions, and pharmaceutical compositions described herein are used to treat obesity in a patient. In one embodiment, the compounds, compositions, and pharmaceutical compositions described herein are used to treat overweight in a patient. In one embodiment, the compounds, compositions, and pharmaceutical compositions described herein are used to treat fatty liver diseases (e.g., non-alcoholic steatohepatitis (NASH), nonalcoholic fatty liver disease (NAFLD) in a patient. In one embodiment, the compounds, compositions, and pharmaceutical compositions described herein are used to treat gastrointestinal diseases (e.g., ulcerative colitis, diarrhea, short bowel syndrome, irritable bowel syndrome, Crohn's disease, gallbladder disease) in a patient.

The compounds, compositions, and pharmaceutical compositions described herein may also be used to reduce body weight; reduce caloric intake; reduce food intake; slow gastric emptying; inhibit gastric acid secretion; lower triglycerides; lower LDL cholesterol; inhibit pancreatic enzyme secretion; and alter body composition (e.g., decrease fat and increase lean muscle). In one embodiment, the compounds, compositions, and pharmaceutical compositions described herein are used to reduce the body weight of a patient.

Each of the diseases and conditions described herein is known in the art and the art-recognized meaning and definition are intended to apply. Such diseases that can be treated with Y receptor agonists are described, for example, in U.S. Pat. No. 7,723,471; US Publication No. 2006/0094653; US Publication No. 2010/0099619; PCT Publication No. WO 2009/138511; PCT Publication No. WO 2011/033068; or PCT Publication No. WO 2011/058165, the disclosures of which are incorporated by reference herein.

EXAMPLES

The following examples are for purposes of illustration and are not intended to limit the scope of the claims.

Example 1

Y receptor agonists having SEQ ID NOs:438, 281 and 439 were synthesized by known methods (e.g., U.S. Pat. No. 7,723,471) and purified by HPLC to a purity greater than 90%.

Example 2

SEQ ID NO:438 in the form of an acetate salt was dissolved in 30 mM, pH 3 phosphate solution with 1.76% glycerol and 0.22% meta-cresol, and aseptically filtered through a 0.22 μm filter. The pH was then adjusted upward to pH 7.2±0.2 with 1 N sodium hydroxide solution. The total weight of the solution was adjusted to the target weight using 30 mM, pH 7.2 phosphate buffer with 1.76% glycerol and 0.22% meta-cresol. A microcrystalline suspension was obtained after stirring at a temperature of about 5° C. for 7 days. The resulting concentration of peptide having SEQ ID NO:438 was 2 mg/mL.

The morphology of the microcrystals was examined under microscope with or without polarized light. The crystals were oval shaped, as shown in FIG. 1. Under polarized light, the crystals exhibited birefringence, as shown in FIG. 2. The shape and surface morphology collected from the microcrystalline suspension were confirmed by SEM. The particle size was determined to be about 5-10 microns. The FTIR spectrum exhibited both alpha-helical and beta-sheet secondary structural characteristics in the solid crystals. Additionally, the FTIR spectrum of the solid crystals showed no significant difference compared to the original fluffy, amorphous powder prior to crystallization.

The skilled artisan will appreciate that microcrystalline suspension with a final concentration of SEQ ID NO:438 in the range of 0.2 mg/mL to 10 mg/mL can be prepared by varying the amount of SEQ ID NO:438 acetate and phosphate buffer.

Example 3

A microcrystalline suspension comprising peptides having SEQ ID NO:281 were prepared as described in Example 2, except that the pH was adjusted from pH 3 upward to a pH between 4 and 5.5. The concentration of peptides having SEQ ID NO:281 in the microcrystalline suspension was 5-10 mg/ml. In this example, a microcrystalline suspension of the peptide having a concentration in the range of 0.2 to 5 mg/mL could be formed at a higher pH range of 5.5 to 7.5 (rather than the pH of 4 to 5.5 that was used).

Example 4

A microcrystalline suspension comprising peptides having SEQ ID NO:439 was prepared as described in Example 2, except that the pH was adjusted from pH 3 upward to a pH from 6.5 to 7.4. The concentration of peptides having SEQ ID NO:439 in the buffered solution was 2 mg/ml.

Example 5

SEQ ID NO:438 acetate was dissolved in 30 mM, pH 3 phosphate solution with 1.76% glycerol and 0.22% meta-cresol, and aseptically filtered through a 0.22 μm filter. Zinc acetate solution was aseptically filtered and added to the solution. The pH was then adjusted upward to pH 7.2±0.2 with 1 N sodium hydroxide solution. The total weight of the solution was adjusted to the target weight using 30 mM, pH 7.2 phosphate buffer with 1.76% glycerol and 0.22% meta-cresol. A zinc-complexed microcrystalline suspension was obtained after constant stirring at a temperature of about 5° C. for 7 days. The final concentration of peptide was 2 mg/mL, and the weight ratio of peptide:zinc was 3:1.

The final concentration of the peptide having SEQ ID NO:438 in the microcrystalline suspension having a range of 0.2-10 mg/mL can be prepared by varying the amount of SEQ ID NO:438 acetate, phosphate buffer, and zinc acetate. Additionally, the weight ratio of peptide:zinc can be modified by varying the amount of zinc added to the solution.

Example 6

The microcrystalline suspensions of SEQ ID NO:438 without zinc (e.g., Example 2) and with zinc (e.g., Example 5) were administered to male Sprague-Dawley rats (12 per formulation) by single subcutaneous injection at 5 mg/kg dose. Vehicle (phosphate buffer) and a solution containing SEQ ID NO:438 were used as controls. Blood samples were collected at various time points from 0.25 to 72 hours post injection. Plasma concentrations of the peptide were determined by an immunoenzymetric assay (IEMA). PK parameters were calculated using WinNonlin Professional software.

Figure 6:
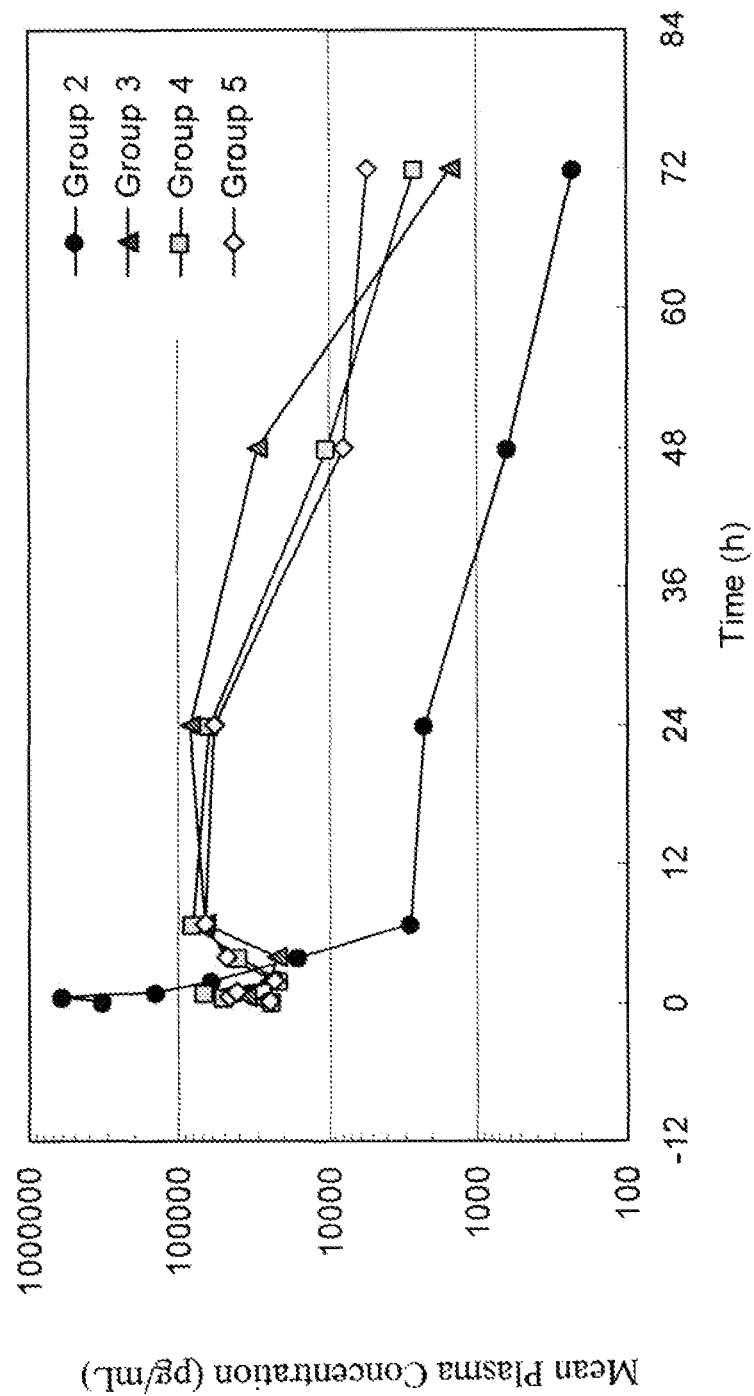
FIG. 6 shows the pK profile (semi-log profile scale) of the following formulations administered to rats: Group 2: a solution containing the peptide of SEQ ID NO:438; Group 3: a microcrystalline suspension containing the peptide of SEQ ID NO:438; Group 4: a zinc-complexed microcrystalline suspension of the peptide of SEQ ID NO:438, where the ratio of peptide:zinc was 3:1; and Group 5: a zinc-complexed microcrystalline suspension of the peptide of SEQ ID NO:438, where the ratio of peptide:zinc was 1:1.
Figure 7:
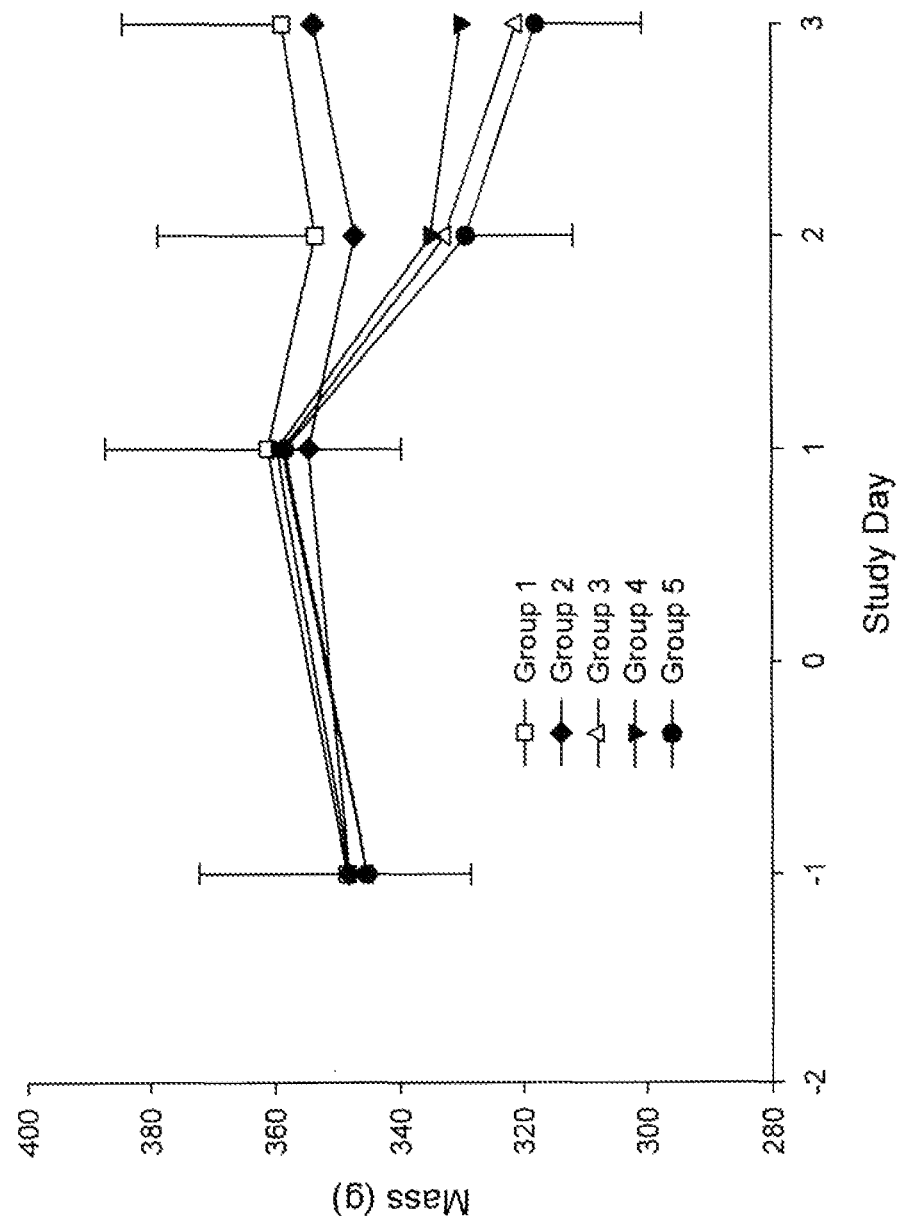
FIG. 7 shows the body weight loss in rats after a single subcutaneous injection (5 mg/kg) of the following formulations: Group 1: vehicle; Group 2: a solution containing the peptide of SEQ ID NO:438; Group 3: a microcrystalline suspension containing the peptide of SEQ ID NO:438; Group 4: a zinc-complexed microcrystalline suspension of the peptide of SEQ ID NO:438, where the ratio of peptide:zinc was 3:1; and Group 5: a zinc-complexed microcrystalline suspension of the peptide of SEQ ID NO:438, where the ratio of peptide:zinc was 1:1.

The results of the pK study are shown in FIG. 6. The results of the body weight study are shown in FIG. 7. With reference to FIGS. 6 and 7: Group 1 was administered a phosphate buffer, pH 7.2, vehicle; Group 2 was administered a solution containing the peptide of SEQ ID NO:438; Group 3 was administered a microcrystalline suspension containing the peptide of SEQ ID NO:438; Group 4 was administered a zinc-complexed microcrystalline suspension of the peptide of SEQ ID NO:438, where the ratio of peptide:zinc was 3:1; and Group 5 was administered a zinc-complexed microcrystalline suspension of the peptide of SEQ ID NO:438, where the ratio of peptide:zinc was 1:1.

FIGS. 6 and 7 demonstrate that the results of rat PK and efficacy studies using microcrystalline suspensions of SEQ ID NO: 438 showed sustained release of the microcrystalline suspensions compared to vehicle and the solution containing SEQ ID NO:438. The mean plasma concentration of the peptide dropped to 2000 pg/mL at 8 hours post injection for the control solution, while it took 72 hours to drop to that same level for the microcrystalline suspensions. The rats that received the microcrystalline suspensions showed approximately 10% more body weight loss than the controls (vehicle and peptide solution) by single subcutaneous injection. The pK profile and weight loss efficacy of the microcrystalline suspension was not statistically significantly different from that of the zinc-complexed microcrystalline suspension.

Example 7

A poly-L-glutamic acid solution was prepared as follows. Poly-L-glutamic acid was dissolved in purified and de-ionized water. The pH was adjusted to pH 7.2 with 1N sodium hydroxide solution.

SEQ ID NO:438 acetate was dissolved in 30 mM, pH 3 phosphate solution with 1.76% glycerol and 0.22% meta-cresol, and aseptically filtered through a 0.22 μm filter. The pH was then adjusted upward to pH 7.2±0.2 with 1 N sodium hydroxide solution. The total weight of the solution was adjusted to the target weight using 30 mM, pH 7.2 phosphate buffer with 1.76%) glycerol and 0.22% meta-cresol. A microcrystalline suspension was obtained after stirring at 5° C. for 7 days.

Thereafter, the poly-L-glutamic acid solution at pH 7.2 was added to the microcrystalline suspension while stirring. Poly-L-glutamic acid-coated microcrystalline suspension was formed after constant stirring at 5° C. for 4 days. The final concentration of peptide was 2 mg/mL and the weight ratio of peptide to poly-L-glutamic acid was 5:1.

Poly-L-glutamic acid-coated microcrystalline suspension with a final concentration of SEQ ID NO:438 in the range of 1-10 mg/mL can be prepared by varying the amount of SEQ ID NO:438 acetate, phosphate buffer, and poly-L-glutamic acid.

Example 8

Figure 8:
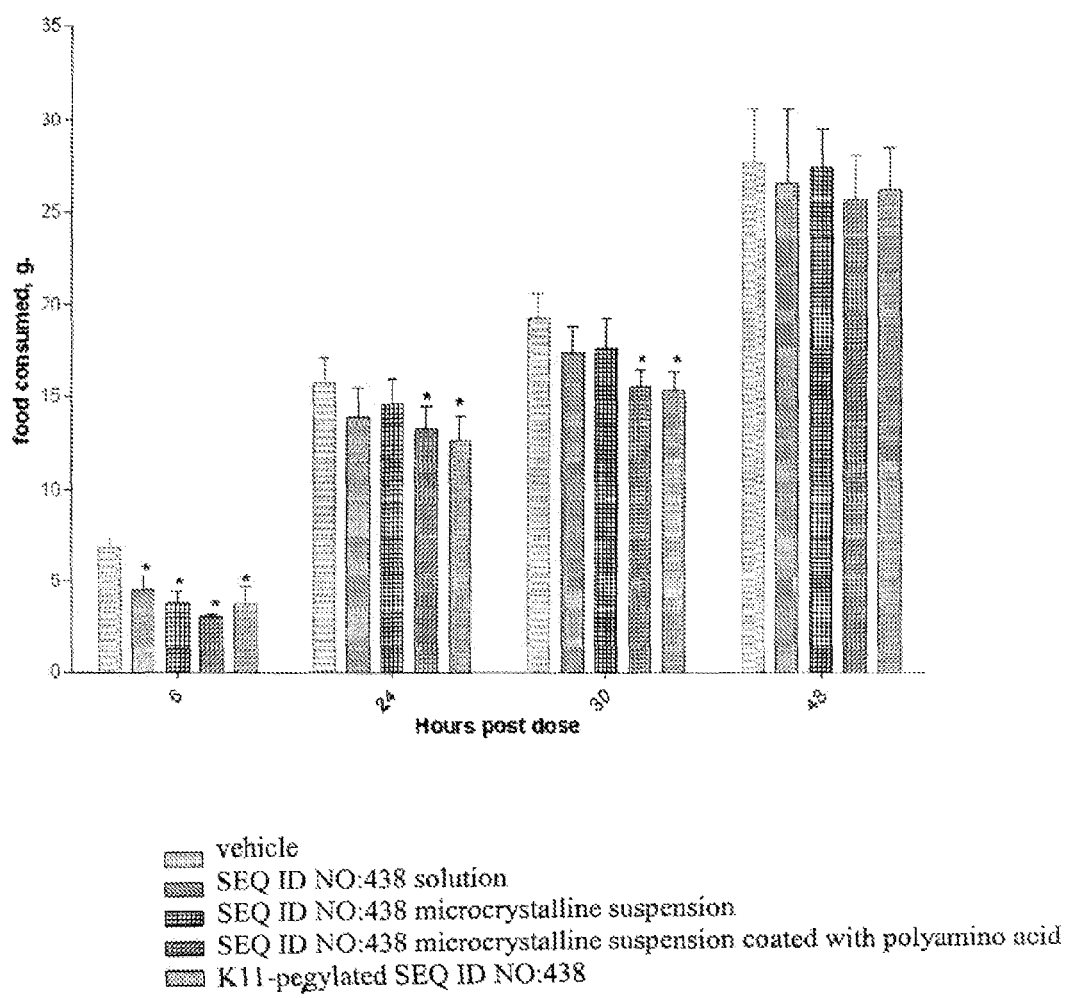
FIG. 8 shows the cumulative food intake on female NH/Swiss mice after a single subcutaneous injection (100 μg/kg) of: (i) vehicle; (ii) a solution containing the peptide of SEQ ID NO:438; (iii) a microcrystalline suspension of the peptide of SEQ ID NO:438; (iv) a poly-L-glutamic acid-coated microcrystalline suspension of peptide of SEQ ID NO:438; and (v) a peptide of SEQ ID NO:438 modified with polyethylene glycol.
Figure 9:
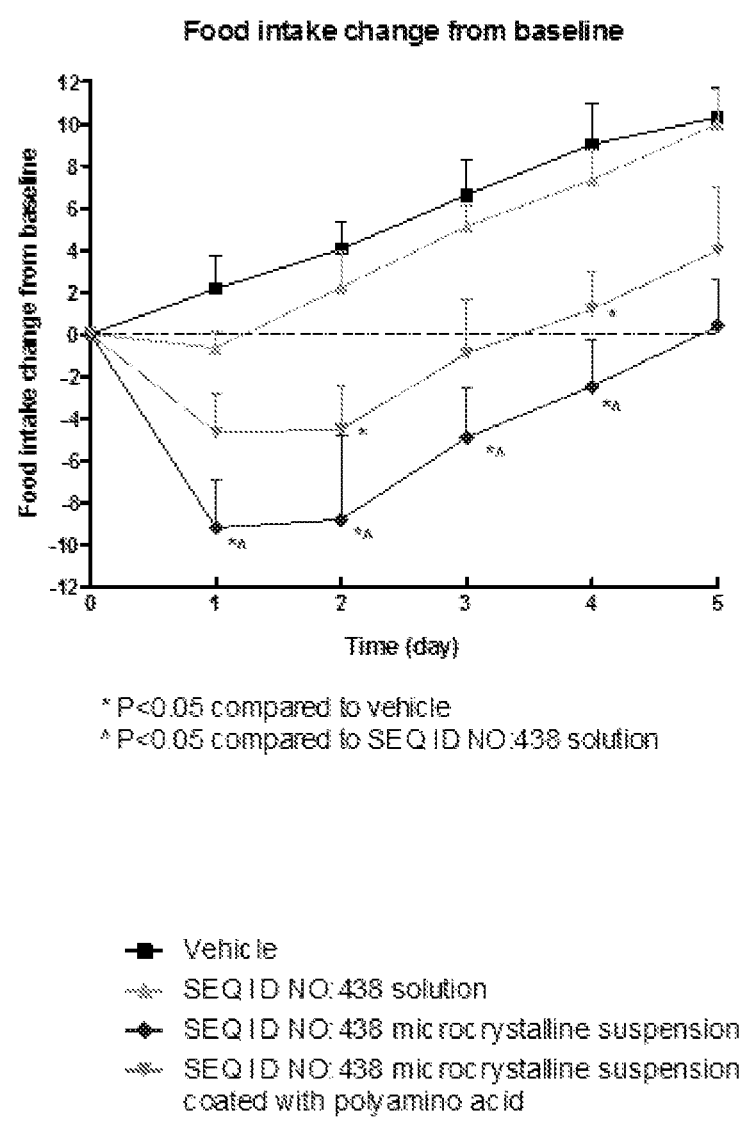
FIG. 9 shows the change from base line of food intake on rats (n=8) following a subcutaneous injection (1 mg/kg) of (i) vehicle; (ii) a solution containing the peptide of SEQ ID NO:438; (iii) a microcrystalline suspension of the peptide of SEQ ID NO:438; (iv) a microcrystalline suspension of peptide of SEQ ID NO:438 coated with poly-L-glutamic acid.

Animal studies were undertaken to compare the formulations described herein for effects on food intake. The following formulations were used: (1) vehicle/placebo containing 30 mM phosphate buffer with 1.76% glycerol at pH 7.2; (ii) solution containing the peptide of SEQ ID NO:438; 4.9% mannitol, 0.07% Tween 80; and a 10 mM acetate buffer, at a pH 4.3; (iii) the microcrystalline suspension of Example 2; (iv) the polyamino acid-coated microcrystalline suspension of Example 7; and (v) a solution of a pegylated peptide, i.e., the peptide of SEQ ID NO:438 modified with $K^{11}$ conjugated to a linear polyethylene glycol having a molecular weight of 20 kilodaltons. The formulations were injected subcutaneously (100 μg/kg) into overnight-fasted female NIH/Swiss mice. Food was introduced immediately after injection and the amount consume was measured at 30 minutes, 60 minutes, 120 minutes, 180 minutes, 240 minutes, 300 minutes, 360 minutes, 24 hours, 30 hours, 48 hours, 56 hours, and 72 hours. The results for cumulative food intake are shown in FIG. 8 (*$p<0.05$ vs. vehicle control; ANOVA, Dunnett's test). The results for the change in food intake from baseline are shown in FIG. 9 (*$p<0.05$ compared to placebo; ^$p<0.05$ compared to solution containing the peptide of SEQ ID NO:438; 4.9% mannitol, 0.07% Tween 80; and a 10 mM acetate buffer, at a pH 4.3).

What is claimed is:

1. A microcrystal comprising a Y receptor agonist peptide, wherein the microcrystal has a particle size of about 1 micron to about 15 microns and is birefringent when viewed under a polarized light microscope, wherein the Y receptor agonist peptide comprises the amino acid sequence of any one of SEQ ID NOs: 1-483.

2. The microcrystal of claim 1, wherein the Y receptor agonist peptide has at least 80% sequence identity to the amino acid sequence of SEQ ID NO:3 (PYY(3-36)):IK-PEAPGEDASPEELNRYYASLRHYLNLVTRQRY.

3. A pharmaceutical composition comprising a plurality of microcrystals according to claim 1.

4. The pharmaceutical composition of claim 3 further comprising an aqueous solution.

5. The pharmaceutical composition of claim 4, further comprising a polyol.

6. The pharmaceutical composition of claim 5, wherein the polyol is glycerol, mannitol, sorbitol, sucrose, glycol, ethylene glycol, pentaerythritol, or a combination thereof.

7. A method for treating diabetes, overweight, obesity, fatty liver disease, a gastrointestinal disease, hypertension, dyslipidemia, cardiovascular disease, a myocardial infarction, atherosclerosis, an eating disorder, or insulin-resistance in a patient in need thereof comprising administering a therapeutically effective amount of the pharmaceutical composition of claim 3.

8. The microcrystal of claim 1, wherein the Y receptor agonist peptide comprises the amino acid sequence of SEQ ID NO:281, 438, 439.

9. The microcrystal of claim 1, wherein the Y receptor agonist peptide comprises the amino acid sequence of SEQ ID NO: 438.

* * * * *

SEQUENCE LISTING

```
<160> NUMBER OF SEQ ID NOS: 483

<210> SEQ ID NO 1
<211> LENGTH: 36
<212> TYPE: PRT
<213> ORGANISM: Homo sapiens

<400> SEQUENCE: 1

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
```

```
                    20                  25                  30

Arg Tyr

<210> SEQ ID NO 4
<211> LENGTH: 36
<212> TYPE: PRT
<213> ORGANISM: Homo sapiens

<400> SEQUENCE: 4

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Tyr
            35

<210> SEQ ID NO 5
<211> LENGTH: 36
<212> TYPE: PRT
<213> ORGANISM: Homo sapiens
<220> FEATURE:
<221> NAME/KEY: MOD_RES
<222> LOCATION: (32)..(32)
<223> OTHER INFORMATION: Aib

<400> SEQUENCE: 5

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ala Xaa
                20                  25                  30

Arg Gln Arg Tyr
            35

<210> SEQ ID NO 6
<211> LENGTH: 36
<212> TYPE: PRT
<213> ORGANISM: Homo sapiens

<400> SEQUENCE: 6

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ile Thr
                20                  25                  30

Arg Gln Arg Tyr
            35

<210> SEQ ID NO 7
<211> LENGTH: 36
<212> TYPE: PRT
<213> ORGANISM: Raja rhina

<400> SEQUENCE: 7

Tyr Pro Pro Lys Pro Glu Ser Pro Gly Glu Asn Ala Thr Pro Glu Glu
1               5                   10                  15

Leu Ala Lys Tyr Ile Ser Ala Asp Arg His Tyr Ile Asn Leu Val Thr
                20                  25                  30

Arg Gln Arg Tyr
            35

<210> SEQ ID NO 8
<211> LENGTH: 34
```

```
<212> TYPE: PRT
<213> ORGANISM: Raja rhina

<400> SEQUENCE: 8

Pro Lys Pro Glu Ser Pro Gly Glu Asn Ala Thr Pro Glu Glu Leu Ala
1               5                   10                  15

Lys Tyr Ile Ser Ala Asp Arg His Tyr Ile Asn Leu Val Thr Arg Gln
            20                  25                  30

Arg Tyr

<210> SEQ ID NO 9
<211> LENGTH: 36
<212> TYPE: PRT
<213> ORGANISM: Danio rerio

<400> SEQUENCE: 9

Ala Pro Pro Lys Pro Glu His Pro Gly Asp Asp Ala Pro Ala Glu Asp
1               5                   10                  15

Val Ala Lys Tyr Tyr Thr Ala Leu Arg His Tyr Ile Asn Leu Ile Thr
            20                  25                  30

Arg Gln Arg Tyr
        35

<210> SEQ ID NO 10
<211> LENGTH: 34
<212> TYPE: PRT
<213> ORGANISM: Danio rerio

<400> SEQUENCE: 10

Pro Lys Pro Glu His Pro Gly Asp Asp Ala Pro Ala Glu Asp Val Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 11
<211> LENGTH: 34
<212> TYPE: PRT
<213> ORGANISM: Raja rhina

<400> SEQUENCE: 11

Pro Lys Pro Glu Asn Pro Gly Glu Asp Ala Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 12
<211> LENGTH: 37
<212> TYPE: PRT
<213> ORGANISM: Gallus gallus

<400> SEQUENCE: 12

Ala Tyr Pro Pro Lys Pro Glu Ser Pro Gly Asp Ala Ala Ser Pro Glu
1               5                   10                  15

Glu Ile Ala Gln Tyr Phe Ser Ala Leu Arg His Tyr Ile Asn Leu Val
            20                  25                  30

Thr Arg Gln Arg Tyr
        35
```

<210> SEQ ID NO 13
<211> LENGTH: 36
<212> TYPE: PRT
<213> ORGANISM: Rana ridibunda

<400> SEQUENCE: 13

Met Pro Pro Lys Pro Asp Asn Pro Ser Ser Asp Ala Ser Pro Glu Glu
1               5                   10                  15

Leu Ser Lys Tyr Met Leu Ala Val Arg Asn Tyr Ile Asn Leu Ile Thr
            20                  25                  30

Arg Gln Arg Tyr
        35

<210> SEQ ID NO 14
<211> LENGTH: 34
<212> TYPE: PRT
<213> ORGANISM: Rana ridibunda

<400> SEQUENCE: 14

Pro Lys Pro Asp Asn Pro Ser Ser Asp Ala Ser Pro Glu Glu Leu Ser
1               5                   10                  15

Lys Tyr Met Leu Ala Val Arg Asn Tyr Ile Asn Leu Ile Thr Arg Gln
            20                  25                  30

Arg Tyr

<210> SEQ ID NO 15
<211> LENGTH: 34
<212> TYPE: PRT
<213> ORGANISM: Ichthyomyzon gagei

<400> SEQUENCE: 15

Pro Lys Pro Asp Asn Pro Gly Asp Asn Ala Ser Pro Glu Gln Met Ala
1               5                   10                  15

Arg Tyr Lys Ala Ala Val Arg His Tyr Ile Asn Leu Ile Thr Arg Gln
            20                  25                  30

Arg Tyr

<210> SEQ ID NO 16
<211> LENGTH: 34
<212> TYPE: PRT
<213> ORGANISM: Raja rhina

<400> SEQUENCE: 16

Pro Lys Pro Glu Asn Pro Gly Asp Asn Ala Ser Pro Glu Glu Met Ala
1               5                   10                  15

Lys Tyr Phe Ser Ala Leu Arg His Tyr Ile Asn Leu Val Thr Arg Gln
            20                  25                  30

Arg Tyr

<210> SEQ ID NO 17
<211> LENGTH: 34
<212> TYPE: PRT
<213> ORGANISM: Rana ridibunda

<400> SEQUENCE: 17

Thr Lys Pro Glu Asn Pro Gly Asn Asp Ala Ser Pro Gln Glu Met Ala
1               5                   10                  15

Lys Tyr Met Thr Ala Leu Arg His Tyr Val Asn Leu Ile Thr Arg Gln
            20                  25                  30

Arg Tyr

<210> SEQ ID NO 18
<211> LENGTH: 36
<212> TYPE: PRT
<213> ORGANISM: Rana ridibunda

<400> SEQUENCE: 18

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
            35

<210> SEQ ID NO 19
<211> LENGTH: 34
<212> TYPE: PRT
<213> ORGANISM: Rana ridibunda

<400> SEQUENCE: 19

Pro Lys Pro Glu Asn Pro Gly Glu Asp Ala Ser Pro Glu Glu Met Thr
1               5                   10                  15

Lys Tyr Leu Thr Ala Leu Arg His Tyr Ile Asn Leu Val Thr Arg Gln
            20                  25                  30

Arg Tyr

<210> SEQ ID NO 20
<211> LENGTH: 34
<212> TYPE: PRT
<213> ORGANISM: Danio rerio

<400> SEQUENCE: 20

Ile Lys Pro Glu Ala Pro Gly Glu Asp Ala Ser Pro Glu Glu Leu Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 21
<211> LENGTH: 34
<212> TYPE: PRT
<213> ORGANISM: Amia calva

<400> SEQUENCE: 21

Ser Lys Pro Asp Asn Pro Gly Glu Asp Ala Pro Ala Glu Asp Met Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 22
<211> LENGTH: 34
<212> TYPE: PRT
<213> ORGANISM: Homo sapiens

<400> SEQUENCE: 22

Pro Lys Pro Glu His Pro Gly Asp Asp Ala Pro Ala Glu Asp Val Asn
1               5                   10                  15

Arg Tyr Tyr Ala Ser Leu Arg His Tyr Leu Asn Leu Val Thr Arg Gln

-continued

```
                20                  25                  30

Arg Tyr

<210> SEQ ID NO 23
<211> LENGTH: 34
<212> TYPE: PRT
<213> ORGANISM: Ovis Aries

<400> SEQUENCE: 23

Pro Lys Pro Glu His Pro Gly Asp Asp Ala Pro Ala Glu Asp Val Asn
1               5                   10                  15

Arg Tyr Tyr Ala Ala Leu Arg Ala Tyr Leu Asn Leu Val Thr Arg Gln
                20                  25                  30

Arg Tyr

<210> SEQ ID NO 24
<211> LENGTH: 34
<212> TYPE: PRT
<213> ORGANISM: Ovis Aries

<400> SEQUENCE: 24

Pro Lys Pro Glu His Pro Gly Asp Asp Ala Pro Ala Glu Asp Val Ala
1               5                   10                  15

Gln Tyr Ala Ala Asp Leu Arg Arg Tyr Ile Asn Met Leu Thr Arg Gln
                20                  25                  30

Arg Tyr

<210> SEQ ID NO 25
<211> LENGTH: 33
<212> TYPE: PRT
<213> ORGANISM: Ovis Aries

<400> SEQUENCE: 25

Ile Pro Glu His Pro Gly Asp Asp Ala Pro Ala Glu Asp Val Ala Arg
1               5                   10                  15

Tyr Tyr Ser Ala Leu Arg Ala Tyr Ile Asn Leu Ile Thr Arg Gln Arg
                20                  25                  30

Tyr

<210> SEQ ID NO 26
<211> LENGTH: 34
<212> TYPE: PRT
<213> ORGANISM: Ovis Aries

<400> SEQUENCE: 26

Pro Lys Pro Glu His Pro Gly Asp Asp Ala Pro Ala Glu Asp Val Ala
1               5                   10                  15

Arg Tyr Tyr Ser Ala Leu Arg His Tyr Ile Asn Leu Ile Thr Arg Gln
                20                  25                  30

Arg Tyr

<210> SEQ ID NO 27
<211> LENGTH: 34
<212> TYPE: PRT
<213> ORGANISM: Ovis Aries

<400> SEQUENCE: 27

Pro Lys Pro Glu His Pro Gly Asp Asp Ala Pro Ala Glu Asp Val Ala
1               5                   10                  15
```

Arg Tyr Tyr Ser Ala Leu Arg Ala Tyr Ile Asn Leu Ile Thr Arg Gln
            20                  25                  30

Arg Tyr

<210> SEQ ID NO 28
<211> LENGTH: 36
<212> TYPE: PRT
<213> ORGANISM: Raja rhina

<400> SEQUENCE: 28

Tyr Pro Pro Lys Pro Glu Ala Pro Gly Glu Asp Ala Ser Pro Glu Glu
1               5                   10                  15

Leu Ala Lys Tyr Tyr Ala Ala Leu Arg His Tyr Ile Asn Leu Val Thr
            20                  25                  30

Arg Gln Arg Tyr
        35

<210> SEQ ID NO 29
<211> LENGTH: 34
<212> TYPE: PRT
<213> ORGANISM: Rana ridibunda

<400> SEQUENCE: 29

Ala Lys Pro Glu Asn Pro Gly Asp Asn Ala Pro Ala Glu Gln Met Ala
1               5                   10                  15

Lys Tyr Leu Thr Ala Leu Arg Ala Tyr Val Asn Leu Ile Thr Arg Gln
            20                  25                  30

Arg Tyr

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Tyr, Ala, Phe, Trp, or absent
<220> FEATURE:
<221> NAME/KEY: MOD_RES
<222> LOCATION: (2)..(2)
<223> OTHER INFORMATION: Pro, Gly, d-Ala, homoPro, hydroxyPro, or absent
<220> FEATURE:
<221> NAME/KEY: MOD_RES
<222> LOCATION: (3)..(3)
<223> OTHER INFORMATION: Ile, Ala, NorVal, Val, Leu, Pro, Ser, Thr, or
      absent
<220> FEATURE:
<221> NAME/KEY: MOD_RES
<222> LOCATION: (4)..(4)
<223> OTHER INFORMATION: Lys, Ala, Gly, Arg, d-Ala, homoLys, homo-Arg,
      Glu Asp, or absent
<220> FEATURE:
<221> NAME/KEY: MOD_RES
<222> LOCATION: (6)..(6)
<223> OTHER INFORMATION: Glu, Ala, Val, Asp, Asn, or Gln
<220> FEATURE:
<221> NAME/KEY: MOD_RES
<222> LOCATION: (7)..(7)
<223> OTHER INFORMATION: Ala, Asn, His, Ser, or Tyr
<220> FEATURE:
<221> NAME/KEY: MOD_RES
<222> LOCATION: (9)..(9)
<223> OTHER INFORMATION: Gly, Ala, Ser, Sarcosine, Pro, or Aib
<220> FEATURE:
<221> NAME/KEY: MOD_RES
<222> LOCATION: (10)..(10)

```
<223> OTHER INFORMATION: Glu, Ala, Asp, Asn, Gln, Pro, Aib, or Gly
<220> FEATURE:
<221> NAME/KEY: MOD_RES
<222> LOCATION: (11)..(11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)..(12)
<223> OTHER INFORMATION: Ala or d-Ala
<220> FEATURE:
<221> NAME/KEY: MOD_RES
<222> LOCATION: (13)..(13)
<223> OTHER INFORMATION: Ser, Ala, Thr, Pro, or homoSer
<220> FEATURE:
<221> NAME/KEY: MOD_RES
<222> LOCATION: (14)..(14)
<223> OTHER INFORMATION: Pro, Ala, homoPro, hydroxyPro, Aib, or Gly
<220> FEATURE:
<221> NAME/KEY: MOD_RES
<222> LOCATION: (15)..(15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)..(16)
<223> OTHER INFORMATION: Glu, Ala, Asp, Asn, or Gln
<220> FEATURE:
<221> NAME/KEY: MOD_RES
<222> LOCATION: (17)..(17)
<223> OTHER INFORMATION: Leu, Ala, Met, Trp, Ile, Val, or NorVal
<220> FEATURE:
<221> NAME/KEY: MOD_RES
<222> LOCATION: (18)..(18)
<223> OTHER INFORMATION: Asn, Asp, Ala, Glu, Gln, Ser, or Thr
<220> FEATURE:
<221> NAME/KEY: MOD_RES
<222> LOCATION: (19)..(19)
<223> OTHER INFORMATION: Arg, Tyr, Lys, Ala, Gln, or N(Me)Ala
<220> FEATURE:
<221> NAME/KEY: MOD_RES
<222> LOCATION: (21)..(21)
<223> OTHER INFORMATION: Tyr, Ala, Met, Phe, or Leu
<220> FEATURE:
<221> NAME/KEY: MOD_RES
<222> LOCATION: (22)..(22)
<223> OTHER INFORMATION: Ala, Ser, Thr, or d-Ala
<220> FEATURE:
<221> NAME/KEY: MOD_RES
<222> LOCATION: (23)..(23)
<223> OTHER INFORMATION: Ser, Ala, Asp, Thr, or homoSer
<220> FEATURE:
<221> NAME/KEY: MOD_RES
<222> LOCATION: (25)..(25)
<223> OTHER INFORMATION: Arg, homoArg, Lys, homoLys, Orn, or Cit
<220> FEATURE:
<221> NAME/KEY: MOD_RES
<222> LOCATION: (26)..(26)
<223> OTHER INFORMATION: His, Ala, Arg, homoArg, homoLys, Orn, or Cit
<220> FEATURE:
<221> NAME/KEY: MOD_RES
<222> LOCATION: (27)..(27)
<223> OTHER INFORMATION: Tyr or Phe
<220> FEATURE:
<221> NAME/KEY: MOD_RES
<222> LOCATION: (28)..(28)
<223> OTHER INFORMATION: Leu, Ile, Val, or Ala
<220> FEATURE:
<221> NAME/KEY: MOD_RES
<222> LOCATION: (29)..(29)
<223> OTHER INFORMATION: Asn or Gln
<220> FEATURE:
<221> NAME/KEY: MOD_RES
<222> LOCATION: (30)..(30)
<223> OTHER INFORMATION: Leu, Ala, NorVal, Val, Ile, or Met
<220> FEATURE:
<221> NAME/KEY: MOD_RES
<222> LOCATION: (31)..(31)
<223> OTHER INFORMATION: Ala, Val, Ile, or Leu
<220> FEATURE:
<221> NAME/KEY: MOD_RES
```

```
<222> LOCATION: (36)..(36)
<223> OTHER INFORMATION: Tyr, N(Me)Tyr, His, Trp, or Phe

<400> SEQUENCE: 30

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Xaa Xaa Xaa Xaa Xaa Xaa Thr
                20                  25                  30

Arg Gln Arg Xaa
            35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 31

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 32

Tyr Pro Ile Lys Pro Ala Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 33

Tyr Pro Ile Lys Pro Glu Ala Pro Ala Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35
```

```
<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 34

Tyr Pro Ile Lys Pro Glu Ala Pro Gly Ala Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 35

Tyr Pro Ile Lys Pro Glu Ala Pro Gly Glu Ala Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 36

Tyr Pro Ile Lys Pro Glu Ala Pro Gly Glu Asp Ala Ala Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 37

Tyr Pro Ile Lys Pro Glu Ala Pro Gly Glu Asp Ala Ser Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 38

Tyr Pro Ile Lys Pro Glu Ala Pro Gly Glu Asp Ala Ser Pro Ala Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 39

Tyr Pro Ile Lys Pro Glu Ala Pro Gly Glu Asp Ala Ser Pro Glu Ala
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 40

Tyr Pro Ile Lys Pro Glu Ala Pro Gly Glu Asp Ala Ser Pro Glu Glu
1               5                   10                  15

Ala Asn Arg Tyr Tyr Ala Ser Leu Arg His Tyr Leu Asn Leu Val Thr
            20                  25                  30

Arg Gln Arg Tyr
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 41

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35

```
<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 42

Tyr Pro Ile Lys Pro Glu Ala Pro Gly Glu Asp Ala Ser Pro Glu Glu
1               5                   10                  15

Leu Asn Lys Tyr Tyr Ala Ser Leu Arg His Tyr Leu Asn Leu Val Thr
            20                  25                  30

Arg Gln Arg Tyr
        35

<210> SEQ ID NO 43
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 43

Tyr Pro Ile Lys Pro Glu Ala Pro Gly Glu Asp Ala Ser Pro Glu Glu
1               5                   10                  15

Leu Asn Arg Tyr Ala Ala Ser Leu Arg His Tyr Leu Asn Leu Val Thr
            20                  25                  30

Arg Gln Arg Tyr
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 44

Tyr Pro Ile Lys Pro Glu Ala Pro Gly Glu Asp Ala Ser Pro Glu Glu
1               5                   10                  15

Leu Asn Arg Tyr Tyr Ala Ala Leu Arg His Tyr Leu Asn Leu Val Thr
            20                  25                  30

Arg Gln Arg Tyr
        35

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 45

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala Tyr Leu Asn Leu Val Thr
            20                  25                  30

Arg Gln Arg Tyr
```

-continued

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 46

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Val Thr
            20                  25                  30

Arg Gln Arg Tyr
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 47

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 48

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 49

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 50

Ala Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 51

Phe Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: d-Ala

<400> SEQUENCE: 52

Tyr Ala Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 53

Tyr Gly Ile Lys Pro Glu Ala Pro Gly Glu Asp Ala Ser Pro Glu Glu

```
                1               5                  10                  15
Leu Asn Arg Tyr Tyr Ala Ser Leu Arg His Tyr Leu Asn Leu Val Thr
                        20                  25                  30

Arg Gln Arg Tyr
        35

<210> SEQ ID NO 54
      <211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 54

Ala Tyr Pro Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
                35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 55

Tyr Ala Pro Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
                35

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 56

Tyr Pro Ala Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
                35

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 57
```

```
Tyr Pro Ile Ala Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 58
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 58

Tyr Pro Ile Lys Ala Pro Glu Ala Pro Gly Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 59

Tyr Pro Ile Lys Pro Ala Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 60

Tyr Pro Ile Lys Pro Glu Ala Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 61
```

```
Tyr Pro Ile Lys Pro Glu Ala Pro Ala Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 62

Tyr Pro Ile Lys Pro Glu Ala Pro Gly Ala Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 63

Tyr Pro Ile Lys Pro Glu Ala Pro Gly Glu Ala Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 64

Tyr Pro Ile Lys Pro Glu Ala Pro Gly Glu Asp Ala Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 65

Tyr Pro Ile Lys Pro Glu Ala Pro Gly Glu Asp Ala Ser Ala Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 66

Tyr Pro Ile Lys Pro Glu Ala Pro Gly Glu Asp Ala Ser Pro Ala Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 67

Tyr Pro Ile Lys Pro Glu Ala Pro Gly Glu Asp Ala Ser Pro Glu Ala
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 68

Tyr Pro Ile Lys Pro Glu Ala Pro Gly Glu Asp Ala Ser Pro Glu Glu
1               5                   10                  15

Ala Leu Asn Arg Tyr Tyr Ala Ser Leu Arg His Tyr Leu Asn Leu Val
            20                  25                  30

Thr Arg Gln Arg Tyr
        35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 69

Tyr Pro Ile Lys Pro Glu Ala Pro Gly Glu Asp Ala Ser Pro Glu Glu
1               5                   10                  15

Leu Ala Asn Arg Tyr Tyr Ala Ser Leu Arg His Tyr Leu Asn Leu Val
            20                  25                  30

Thr Arg Gln Arg Tyr
            35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Tyr Pro Ile Lys Pro Glu Ala Pro Gly Glu Asp Ala Ser Pro Glu Glu
1               5                   10                  15

Leu Asn Ala Arg Tyr Tyr Ala Ser Leu Arg His Tyr Leu Asn Leu Val
            20                  25                  30

Thr Arg Gln Arg Tyr
            35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 71

Tyr Pro Ile Lys Pro Glu Ala Pro Gly Glu Asp Ala Ser Pro Glu Glu
1               5                   10                  15

Leu Asn Arg Ala Tyr Tyr Ala Ser Leu Arg His Tyr Leu Asn Leu Val
            20                  25                  30

Thr Arg Gln Arg Tyr
            35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 72

Tyr Pro Ile Lys Pro Glu Ala Pro Gly Glu Asp Ala Ser Pro Glu Glu
1               5                   10                  15

Leu Asn Arg Tyr Ala Tyr Ala Ser Leu Arg His Tyr Leu Asn Leu Val
            20                  25                  30

Thr Arg Gln Arg Tyr
            35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
```

-continued peptide construct

<400> SEQUENCE: 73

Tyr Pro Ile Lys Pro Glu Ala Pro Gly Glu Asp Ala Ser Pro Glu Glu
1               5                   10                  15

Leu Asn Arg Tyr Tyr Ala Ala Ser Leu Arg His Tyr Leu Asn Leu Val
            20                  25                  30

Thr Arg Gln Arg Tyr
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 74

Tyr Pro Ile Lys Pro Glu Ala Pro Gly Glu Asp Ala Ser Pro Glu Glu
1               5                   10                  15

Leu Asn Arg Tyr Tyr Ala Ser Ala Leu Arg His Tyr Leu Asn Leu Val
            20                  25                  30

Thr Arg Gln Arg Tyr
        35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 75

Tyr Pro Ile Lys Pro Glu Ala Pro Gly Glu Asp Ala Ser Pro Glu Glu
1               5                   10                  15

Leu Asn Arg Tyr Tyr Ala Ser Leu Ala Arg His Tyr Leu Asn Leu Val
            20                  25                  30

Thr Arg Gln Arg Tyr
        35

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 76

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala His Tyr Leu Asn Leu Val
            20                  25                  30

Thr Arg Gln Arg Tyr
        35

<210> SEQ ID NO 77
<211> LENGTH: 37
<212> TYPE: PRT
<213> ORGANISM: Artificial Sequence
<220> FEATURE:

```
<223> OTHER INFORMATION: Description of Artificial Sequence: Synthetic
      peptide construct

<400> SEQUENCE: 77

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Ala Tyr Leu Asn Leu Val
            20                  25                  30

Thr Arg Gln Arg Tyr
        35

<210> SEQ ID NO 78
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 78

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Ala Leu Asn Leu Val
            20                  25                  30

Thr Arg Gln Arg Tyr
        35

<210> SEQ ID NO 79
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 79

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Ala Asn Leu Val
            20                  25                  30

Thr Arg Gln Arg Tyr
        35

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 80

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Leu Val
            20                  25                  30

Thr Arg Gln Arg Tyr
        35

<210> SEQ ID NO 81
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      peptide construct

<400> SEQUENCE: 81

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Ala Val
            20                  25                  30

Thr Arg Gln Arg Tyr
        35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 82

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Ala
            20                  25                  30

Thr Arg Gln Arg Tyr
        35

<210> SEQ ID NO 83
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 83

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Ala Arg Gln Arg Tyr
        35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 84

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Ala Gln Arg Tyr
        35

<210> SEQ ID NO 85
<211> LENGTH: 37
<212> TYPE: PRT
```

<213> ORGANISM: Artificial Sequence
<220> FEATURE:
<223> OTHER INFORMATION: Description of Artificial Sequence: Synthetic
     peptide construct

<400> SEQUENCE: 85

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Ala Arg Tyr
        35

<210> SEQ ID NO 86
<211> LENGTH: 37
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 86

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Ala Tyr
        35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 87

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr Ala
        35

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
     peptide construct
<220> FEATURE:
<221> NAME/KEY: MOD_RES
<222> LOCATION: (1)..(1)
<223> OTHER INFORMATION: Tyr, Ala, Phe, Trp, or absent
<220> FEATURE:
<221> NAME/KEY: MOD_RES
<222> LOCATION: (2)..(2)
<223> OTHER INFORMATION: Pro, Gly, d-Ala, homoPro, hydroxy-Pro, or
     absent
<220> FEATURE:
<221> NAME/KEY: MOD_RES
<222> LOCATION: (3)..(3)
<223> OTHER INFORMATION: Ile, Ala, NorVal, Val, Leu, Pro, Ser, or Thr
<220> FEATURE:
<221> NAME/KEY: MOD_RES

```
<222> LOCATION: (4)..(4)
<223> OTHER INFORMATION: Lys, Ala, Gly, Arg, d-Ala, homoLys, homoArg,
      Glu, or Asp
<220> FEATURE:
<221> NAME/KEY: MOD_RES
<222> LOCATION: (6)..(6)
<223> OTHER INFORMATION: Glu, Ala, Val, Asp, Asn, or Gln
<220> FEATURE:
<221> NAME/KEY: MOD_RES
<222> LOCATION: (7)..(7)
<223> OTHER INFORMATION: Ala, Asn, His, Ser, or Tyr
<220> FEATURE:
<221> NAME/KEY: MOD_RES
<222> LOCATION: (9)..(9)
<223> OTHER INFORMATION: Gly, Ala, Ser, Sarcosine, Pro, or Aib
<220> FEATURE:
<221> NAME/KEY: MOD_RES
<222> LOCATION: (10)..(10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)..(11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)..(12)
<223> OTHER INFORMATION: Ala or d-Ala
<220> FEATURE:
<221> NAME/KEY: MOD_RES
<222> LOCATION: (13)..(13)
<223> OTHER INFORMATION: Ser, Ala, Thr, or homoSer
<220> FEATURE:
<221> NAME/KEY: MOD_RES
<222> LOCATION: (14)..(14)
<223> OTHER INFORMATION: Pro, Ala, homoPro, hydroxyPro, Aib, or Gly
<220> FEATURE:
<221> NAME/KEY: MOD_RES
<222> LOCATION: (15)..(15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)..(16)
<223> OTHER INFORMATION: Glu, Ala, Asp, Asn, or Gln
<220> FEATURE:
<221> NAME/KEY: MOD_RES
<222> LOCATION: (17)..(17)
<223> OTHER INFORMATION: Leu, Ala, Met, Trp, Ile, Val, or NorVal
<220> FEATURE:
<221> NAME/KEY: MOD_RES
<222> LOCATION: (18)..(18)
<223> OTHER INFORMATION: Asn, Asp, Ala, Glu, Gln, Ser, or Thr
<220> FEATURE:
<221> NAME/KEY: MOD_RES
<222> LOCATION: (19)..(19)
<223> OTHER INFORMATION: Arg, Tyr, Lys, Ala, Gln, or N(Me)Ala
<220> FEATURE:
<221> NAME/KEY: MOD_RES
<222> LOCATION: (21)..(21)
<223> OTHER INFORMATION: Tyr, Ala, Met, Phe, or Leu
<220> FEATURE:
<221> NAME/KEY: MOD_RES
<222> LOCATION: (22)..(22)
<223> OTHER INFORMATION: Ala, Ser, Thr, or d-Ala
<220> FEATURE:
<221> NAME/KEY: MOD_RES
<222> LOCATION: (23)..(23)
<223> OTHER INFORMATION: Ser, Ala, Thr, or homoSer
<220> FEATURE:
<221> NAME/KEY: MOD_RES
<222> LOCATION: (26)..(26)
<223> OTHER INFORMATION: His or Ala
<220> FEATURE:
<221> NAME/KEY: MOD_RES
<222> LOCATION: (28)..(28)
<223> OTHER INFORMATION: Leu, Ile, Val, or Ala
<220> FEATURE:
<221> NAME/KEY: MOD_RES
<222> LOCATION: (30)..(30)
<223> OTHER INFORMATION: Leu, Ala, NorVal, Val, Ile, or Met
```

```
<220> FEATURE:
<221> NAME/KEY: MOD_RES
<222> LOCATION: (31)..(31)
<223> OTHER INFORMATION: Ala, Val, Ile, or Leu
<220> FEATURE:
<221> NAME/KEY: MOD_RES
<222> LOCATION: (36)..(36)
<223> OTHER INFORMATION: Tyr, N(Me)Tyr, His, Trp, or Phe

<400> SEQUENCE: 88

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 89
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 89

Ala Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 90
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 90

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 91

Ile Gly Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 92
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: d-Ala

<400> SEQUENCE: 92

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 93

Ile Lys Ala Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 94
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 94

Ile Lys Pro Ala Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: d-Ala

<400> SEQUENCE: 95

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30
```

Arg Tyr

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 96

Ile Lys Pro Glu Ala Ala Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 97
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 97

Ile Lys Pro Glu Ala Pro Ala Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 98
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 98

Ile Lys Pro Glu Ala Pro Gly Ala Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 99

Ile Lys Pro Glu Ala Pro Gly Glu Ala Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence: Synthetic
    peptide construct
<220> FEATURE:
<221> NAME/KEY: MOD_RES
<222> LOCATION: (10)..(10)
<223> OTHER INFORMATION: d-Ala

<400> SEQUENCE: 100

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence: Synthetic
    peptide construct

<400> SEQUENCE: 101

Ile Lys Pro Glu Ala Pro Gly Glu Asp Ala Ala Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence: Synthetic
    peptide construct

<400> SEQUENCE: 102

Ile Lys Pro Glu Ala Pro Gly Glu Asp Ala Ser Ala Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 103
<211> LENGTH: 34
<212> TYPE: PRT
<213> ORGANISM: Artificial Sequence
<220> FEATURE:
<223> OTHER INFORMATION: Description of Artificial Sequence: Synthetic
    peptide construct

<400> SEQUENCE: 103

Ile Lys Pro Glu Ala Pro Gly Glu Asp Ala Ser Pro Ala Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 104
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 104

Ile Lys Pro Glu Ala Pro Gly Glu Asp Ala Ser Pro Glu Ala Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 105
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 105

Ile Lys Pro Glu Ala Pro Gly Glu Asp Ala Ser Pro Glu Glu Ala Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 106
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 106

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 107
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 107

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 108

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 108

Ile Lys Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 109
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: (NMe)Ala

<400> SEQUENCE: 109

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 110
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 110

Ile Lys Pro Glu Ala Pro Gly Glu Asp Ala Ser Pro Glu Glu Leu Asn
1               5                   10                  15

Arg Ala Tyr Ala Ser Leu Arg His Tyr Leu Asn Leu Val Thr Arg Gln
            20                  25                  30

Arg Tyr

<210> SEQ ID NO 111
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 111

Ile Lys Pro Glu Ala Pro Gly Glu Asp Ala Ser Pro Glu Glu Leu Asn
1               5                   10                  15

Arg Tyr Ala Ala Ser Leu Arg His Tyr Leu Asn Leu Val Thr Arg Gln
            20                  25                  30

Arg Tyr
```

```
<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (20)..(20)
<223> OTHER INFORMATION: d-Ala

<400> SEQUENCE: 112

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 113

Ile Lys Pro Glu Ala Pro Gly Glu Asp Ala Ser Pro Glu Glu Leu Asn
1               5                   10                  15

Arg Tyr Tyr Ala Ala Leu Arg His Tyr Leu Asn Leu Val Thr Arg Gln
            20                  25                  30

Arg Tyr

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 114

Ile Lys Pro Glu Ala Pro Gly Glu Asp Ala Ser Pro Glu Glu Leu Asn
1               5                   10                  15

Arg Tyr Tyr Ala Ser Ala Arg His Tyr Leu Asn Leu Val Thr Arg Gln
            20                  25                  30

Arg Tyr

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 115

Ile Lys Pro Glu Ala Pro Gly Glu Asp Ala Ser Pro Glu Glu Leu Asn
1               5                   10                  15

Arg Tyr Tyr Ala Ser Leu Ala His Tyr Leu Asn Leu Val Thr Arg Gln
            20                  25                  30

Arg Tyr
```

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 116

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Tyr

<210> SEQ ID NO 117
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 117

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 118

Ile Lys Pro Glu Ala Pro Gly Glu Asp Ala Ser Pro Glu Glu Leu Asn
1               5                   10                  15

Arg Tyr Tyr Ala Ser Leu Arg His Ala Leu Asn Leu Val Thr Arg Gln
            20                  25                  30

Arg Tyr

<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 119

Ile Lys Pro Glu Ala Pro Gly Glu Asp Ala Ser Pro Glu Glu Leu Asn
1               5                   10                  15

Arg Tyr Tyr Ala Ser Leu Arg His Tyr Ala Asn Leu Val Thr Arg Gln
            20                  25                  30

Arg Tyr

<210> SEQ ID NO 120
<211> LENGTH: 34

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 120

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Ala Leu Val Thr Arg Gln
            20                  25                  30

Arg Tyr

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 121

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Ala Val Thr Arg Gln
            20                  25                  30

Arg Tyr

<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 122

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ala Thr Arg Gln
            20                  25                  30

Arg Tyr

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 123

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Ala Arg Gln
            20                  25                  30

Arg Tyr

<210> SEQ ID NO 124
<211> LENGTH: 34
<212> TYPE: PRT
<213> ORGANISM: Artificial Sequence
<220> FEATURE:
```

<223> OTHER INFORMATION: Description of Artificial Sequence: Synthetic
      peptide construct

<400> SEQUENCE: 124

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Ala Gln
            20                  25                  30

Arg Tyr

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 125

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Lys Gln
            20                  25                  30

Arg Tyr

<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 126

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Ala
            20                  25                  30

Arg Tyr

<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 127

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Ala Tyr

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

```
<400> SEQUENCE: 128

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Ala

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 129

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 130

Pro Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 131

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (1)..(1)
<223> OTHER INFORMATION: Ac-Pro

<400> SEQUENCE: 132

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: (NMe)Tyr

<400> SEQUENCE: 133

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 134

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg His

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 135

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg His

<210> SEQ ID NO 136
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 136

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Trp

<210> SEQ ID NO 137
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 137

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Phe

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 138

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Phe

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Tyr(CH2SO3)

<400> SEQUENCE: 139

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 140
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Pro(OH)

<400> SEQUENCE: 140

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Pro

<210> SEQ ID NO 141
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (33)..(33)
<223> OTHER INFORMATION: homo-Arg

<400> SEQUENCE: 141

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 142

Ile Lys Pro Glu Ala Pro Gly Glu Asp Ala Ser Ala Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 143

Ile Lys Pro Glu Ala Pro Gly Glu Asp Ala Ser Pro Glu Glu Leu Ala
1               5                   10                  15

Arg Tyr Tyr Ala Ser Leu Arg Ala Tyr Leu Asn Leu Val Thr Arg Gln
            20                  25                  30
```

-continued

Arg Tyr

<210> SEQ ID NO 144
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 144

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 145
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 145

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 146
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)..(11)
<223> OTHER INFORMATION: Ser(Ac)

<400> SEQUENCE: 146

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)..(21)

<223> OTHER INFORMATION: Ser(Ac)

<400> SEQUENCE: 147

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: homo-Arg

<400> SEQUENCE: 148

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (23)..(23)
<223> OTHER INFORMATION: homo-Arg

<400> SEQUENCE: 149

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: FmocSO3H-Ile
<220> FEATURE:
<221> NAME/KEY: MOD_RES
<222> LOCATION: (2)..(2)
<223> OTHER INFORMATION: Lys(FmocSO3H)

<400> SEQUENCE: 150

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile

<400> SEQUENCE: 151

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile

<400> SEQUENCE: 152

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 153
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isobutyloxycarbonyl-Ile

<400> SEQUENCE: 153

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 154
<211> LENGTH: 34
<212> TYPE: PRT

-continued

```
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isopropyloxycarbonyl-Ile

<400> SEQUENCE: 154

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 155
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: N-butyloxycarbonyl-Ile

<400> SEQUENCE: 155

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Ethoxycarbonyl-Ile

<400> SEQUENCE: 156

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 157
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 157

Ile Lys Pro Glu Ala Pro Gly Glu Asp Ala Ser Pro Glu Glu Leu Ser
1               5                   10                  15
```

```
Arg Tyr Tyr Ala Ser Leu Arg His Tyr Leu Asn Leu Val Thr Arg Gln
            20                  25                  30

Arg Tyr

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (16)..(16)
<223> OTHER INFORMATION: NorVal

<400> SEQUENCE: 158

Ile Lys Pro Glu Ala Pro Gly Glu Asp Ala Ser Pro Glu Glu Leu Xaa
1               5                   10                  15

Arg Tyr Tyr Ala Ser Leu Arg His Tyr Leu Asn Leu Val Thr Arg Gln
            20                  25                  30

Arg Tyr

<210> SEQ ID NO 159
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 159

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 160
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile
<220> FEATURE:
<221> NAME/KEY: MOD_RES
<222> LOCATION: (2)..(2)
<223> OTHER INFORMATION: homo-Lys

<400> SEQUENCE: 160

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr
```

```
<210> SEQ ID NO 161
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: homo-Arg

<400> SEQUENCE: 161

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 162
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile
<220> FEATURE:
<221> NAME/KEY: MOD_RES
<222> LOCATION: (17)..(17)
<223> OTHER INFORMATION: homo-Arg

<400> SEQUENCE: 162

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys
<220> FEATURE:
<221> NAME/KEY: MOD_RES
<222> LOCATION: (17)..(17)
<223> OTHER INFORMATION: homo-Arg

<400> SEQUENCE: 163

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 164
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile
<220> FEATURE:
<221> NAME/KEY: MOD_RES
<222> LOCATION: (2)..(2)
<223> OTHER INFORMATION: homo-Lys
<220> FEATURE:
<221> NAME/KEY: MOD_RES
<222> LOCATION: (17)..(17)
<223> OTHER INFORMATION: homo-Arg

<400> SEQUENCE: 164

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 165
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 165

Ile Lys Pro Glu Ala Pro Gly Glu Asp Ala Ser Pro Glu Glu Met Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 166
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 166

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 167
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
```

```
<221> NAME/KEY: MOD_RES
<222> LOCATION: (2)..(2)
<223> OTHER INFORMATION: homo-Lys
<220> FEATURE:
<221> NAME/KEY: MOD_RES
<222> LOCATION: (17)..(17)
<223> OTHER INFORMATION: homo-Arg

<400> SEQUENCE: 167

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 168
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys
<220> FEATURE:
<221> NAME/KEY: MOD_RES
<222> LOCATION: (11)..(11)
<223> OTHER INFORMATION: homo-Ser
<220> FEATURE:
<221> NAME/KEY: MOD_RES
<222> LOCATION: (17)..(17)
<223> OTHER INFORMATION: homo-Arg

<400> SEQUENCE: 168

Leu Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 169
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 169

Ile Lys Pro Glu Ala Pro Gly Glu Asp Ala Ser Ala Gln Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 170
<211> LENGTH: 35
<212> TYPE: PRT
<213> ORGANISM: Artificial Sequence
<220> FEATURE:
<223> OTHER INFORMATION: Description of Artificial Sequence: Synthetic
``` peptide construct

<400> SEQUENCE: 170

Ile Lys Ala Pro Glu Ala Pro Gly Glu Asp Ala Ser Pro Glu Glu Leu
1               5                   10                  15

Asn Arg Tyr Tyr Ala Ser Leu Lys His Tyr Leu Asn Leu Val Thr Arg
            20                  25                  30

Gln Arg Tyr
        35

<210> SEQ ID NO 171
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 171

Ile Lys Pro Glu Cys Pro Gly Glu Asp Ala Ser Pro Glu Glu Cys Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 172
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 172

Leu Glu Pro Val Tyr Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 173
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 173

Leu Glu Pro Val Tyr Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 174
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct -continued

<400> SEQUENCE: 174

Ile Lys Pro Glu Ala Pro Gly Glu Asp Ala Ser Pro Glu Glu Leu Asn
1               5                   10                  15

Arg Tyr Tyr Tyr Ala Ser Leu Arg His Tyr Leu Asn Ala Val Thr Arg
            20                  25                  30

Gln Arg Tyr
        35

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 175

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 176
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 176

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 177
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 177

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 178

Tyr Tyr Ala Ser Leu Arg His Tyr Leu Asn Leu Val Thr Arg Gln Arg
1               5                   10                  15

Tyr

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 179

Arg His Tyr Leu Asn Leu Val Thr Arg Gln Arg Tyr
1               5                   10

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: Aca

<400> SEQUENCE: 180

Tyr Pro Ile Lys Xaa Pro Glu Glu Leu Asn Arg Tyr Tyr Ala Ser Leu
1               5                   10                  15

Arg His Tyr Leu Asn Leu Val Thr Arg Gln Arg Tyr
            20                  25

<210> SEQ ID NO 181
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: Aca

<400> SEQUENCE: 181

Tyr Pro Ile Lys Xaa Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: Aca

<400> SEQUENCE: 182

Tyr Pro Ile Lys Xaa Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 183
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: Aca

<400> SEQUENCE: 183

Tyr Pro Ile Lys Xaa Ala Ser Leu Arg His Tyr Leu Asn Leu Val Thr
1               5                   10                  15

Arg Gln Arg Tyr
            20

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)..(5)
<223> OTHER INFORMATION: Aca

<400> SEQUENCE: 184

Tyr Pro Ile Lys Xaa Arg His Tyr Leu Asn Leu Val Thr Arg Gln Arg
1               5                   10                  15

Tyr

<210> SEQ ID NO 185
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 185

Tyr Pro Ile Lys Pro Glu Ala Pro Gly Glu Ala Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)..(11)
<223> OTHER INFORMATION: Ado

<400> SEQUENCE: 186

Tyr Pro Ile Lys Pro Glu Ala Pro Gly Glu Xaa Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 187
<211> LENGTH: 34
```

-continued

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile
<220> FEATURE:
<221> NAME/KEY: MOD_RES
<222> LOCATION: (2)..(2)
<223> OTHER INFORMATION: Lys(PEG5000)

<400> SEQUENCE: 187

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Lys(PEG5000)

<400> SEQUENCE: 188

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 189
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile
<220> FEATURE:
<221> NAME/KEY: MOD_RES
<222> LOCATION: (17)..(17)
<223> OTHER INFORMATION: Lys(PEG5000)

<400> SEQUENCE: 189

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 190
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: PEG5000-Ile

<400> SEQUENCE: 190

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 191
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)..(11)
<223> OTHER INFORMATION: Ser(OAc)

<400> SEQUENCE: 191

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)..(21)
<223> OTHER INFORMATION: Ser(OAc)

<400> SEQUENCE: 192

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 193
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile
<220> FEATURE:
<221> NAME/KEY: MOD_RES
<222> LOCATION: (17)..(17)
```

<223> OTHER INFORMATION: Lys(Oct)

<400> SEQUENCE: 193

```
Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr
```

<210> SEQ ID NO 194
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: Lys(Oct)

<400> SEQUENCE: 194

```
Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr
```

<210> SEQ ID NO 195
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Octanoic acid-Ile

<400> SEQUENCE: 195

```
Ile Ala Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 196
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile
<220> FEATURE:
<221> NAME/KEY: MOD_RES
<222> LOCATION: (17)..(17)
<223> OTHER INFORMATION: Lys(stearyl)

<400> SEQUENCE: 196

```
Ile Ala Pro Glu Ala Pro Gly Glu Asp Ala Ser Pro Glu Glu Leu Asn
1               5                   10                  15
```

```
Lys Tyr Tyr Ala Ser Leu Arg His Tyr Leu Asn Leu Val Thr Arg Gln
            20                  25                  30

Arg Tyr

<210> SEQ ID NO 197
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: Lys(stearyl)

<400> SEQUENCE: 197

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Ac-Glu

<400> SEQUENCE: 198

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 199
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Stearyl-Glu

<400> SEQUENCE: 199

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 200
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (1)..(1)
<223> OTHER INFORMATION: Octyl-Glu

<400> SEQUENCE: 200

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 201
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Succinyl-Glu

<400> SEQUENCE: 201

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Stearyl-Ala

<400> SEQUENCE: 202

Ala Ser Leu Arg His Tyr Leu Asn Leu Val Thr Arg Gln Arg Tyr
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Octyl-Ala

<400> SEQUENCE: 203

Ala Ser Leu Arg His Tyr Leu Asn Leu Val Thr Arg Gln Arg Tyr
1               5                   10                  15

<210> SEQ ID NO 204
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
```

```
<221> NAME/KEY: MOD_RES
<222> LOCATION: (14)..(14)
<223> OTHER INFORMATION: Lys(PEG)

<400> SEQUENCE: 204

Ile Ala Pro Glu Ala Pro Gly Glu Asp Ala Ser Pro Glu Lys Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 205
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)..(14)
<223> OTHER INFORMATION: Lys(Oct)

<400> SEQUENCE: 205

Ile Ala Pro Glu Ala Pro Gly Glu Asp Ala Ser Pro Glu Lys Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 206
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Ile
<220> FEATURE:
<221> NAME/KEY: MOD_RES
<222> LOCATION: (14)..(14)
<223> OTHER INFORMATION: Lys(Oct)

<400> SEQUENCE: 206

Ile Ala Pro Glu Ala Pro Gly Glu Asp Ala Ser Pro Glu Lys Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 207
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Tyr(8-Am-3,6-dioxaoct)

<400> SEQUENCE: 207
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 208
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Tyr(11-Am-undecanoyl)

<400> SEQUENCE: 208

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Tyr(12 Ado)

<400> SEQUENCE: 209

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 210
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)..(34)
<223> OTHER INFORMATION: Tyr(8-Oct)

<400> SEQUENCE: 210

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 211

```
<211> LENGTH: 5
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 352

<400> SEQUENCE: 211

Ile Lys Pro Glu Ala
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 353

<400> SEQUENCE: 212

Ile Lys Pro Glu Ala Pro
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 354

<400> SEQUENCE: 213

Ile Lys Pro Glu Ala Pro Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 355

<400> SEQUENCE: 214

Ile Lys Pro Glu Ala Pro Gly Glu
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 356

<400> SEQUENCE: 215

Ile Lys Pro Glu Ala Pro Gly Glu Asp
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 357

<400> SEQUENCE: 216
```

```
Ile Lys Pro Glu Ala Pro Gly Glu Asp Ala
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: C-term
      Mimic A linker to SEQ ID NO: 358

<400> SEQUENCE: 217

Ile Lys Pro Glu Ala Pro Gly Glu Asp Ala Ser
1               5                   10

<210> SEQ ID NO 218
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (7)..(7)
<223> OTHER INFORMATION: Aib

<400> SEQUENCE: 218

Ile Lys Pro Glu Ala Ala Xaa Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)..(8)
<223> OTHER INFORMATION: Aib

<400> SEQUENCE: 219

Ile Lys Pro Glu Ala Pro Ala Xaa Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 220
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)..(9)
<223> OTHER INFORMATION: Aib

<400> SEQUENCE: 220

Ile Lys Pro Glu Ala Pro Gly Ala Xaa Ala Ser Pro Glu Glu Leu Asn
```

```
1               5                   10                  15
Arg Tyr Tyr Ala Ser Leu Arg His Tyr Leu Asn Leu Val Thr Arg Gln
            20                  25                  30

Arg Tyr

<210> SEQ ID NO 221
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)..(10)
<223> OTHER INFORMATION: Aib

<400> SEQUENCE: 221

Ile Lys Pro Glu Ala Pro Gly Glu Ala Xaa Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)..(11)
<223> OTHER INFORMATION: Aib

<400> SEQUENCE: 222

Ile Lys Pro Glu Ala Pro Gly Glu Asp Ala Xaa Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 223
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (12)..(12)
<223> OTHER INFORMATION: Aib

<400> SEQUENCE: 223

Ile Lys Pro Glu Ala Pro Gly Glu Asp Ala Ala Xaa Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 224
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)..(13)
<223> OTHER INFORMATION: Aib

<400> SEQUENCE: 224

Ile Lys Pro Glu Ala Pro Gly Glu Asp Ala Ser Ala Xaa Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 225
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 225

Ile Lys Pro Glu Ala Ala Pro Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 226
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 226

Ile Lys Pro Glu Ala Pro Ala Pro Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 227
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 227

Ile Lys Pro Glu Ala Pro Gly Ala Pro Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 228
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 228

Ile Lys Pro Glu Ala Pro Gly Glu Ala Pro Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 229

Ile Lys Pro Glu Ala Pro Gly Glu Asp Ala Pro Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 230
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 230

Ile Lys Pro Glu Ala Pro Gly Glu Asp Ala Ser Ala Pro Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 359

<400> SEQUENCE: 231

Ile Lys Pro Glu Ala
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 360

<400> SEQUENCE: 232
```

```
Ile Lys Pro Glu Ala Pro
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 361

<400> SEQUENCE: 233

Ile Lys Pro Glu Ala Pro Gly
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 362

<400> SEQUENCE: 234

Ile Lys Pro Glu Ala Pro Gly Glu
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 363

<400> SEQUENCE: 235

Ile Lys Pro Glu Ala Pro Gly Glu Asp
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 364

<400> SEQUENCE: 236

Ile Lys Pro Glu Ala Pro Gly Glu Asp Ala
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: C-term
      Mimic B linker to SEQ ID NO: 365

<400> SEQUENCE: 237

Ile Lys Pro Glu Ala Pro Gly Glu Asp Ala Ser
1               5                   10

<210> SEQ ID NO 238
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      peptide construct

<400> SEQUENCE: 238

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 239
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 239

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 240
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 240

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 241
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 241

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 242
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile

<400> SEQUENCE: 242

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 243
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 243

Ile Pro Glu Ala Pro Gly Glu Asp Ala Ser Pro Glu Glu Leu Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 244
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 244

Tyr Pro Ile Pro Glu Ala Pro Gly Glu Asp Ala Ser Ala Glu Glu Leu
1               5                   10                  15

Ala Arg Tyr Tyr Ser Ala Leu Arg Ala Tyr Ile Asn Leu Ile Thr Arg
            20                  25                  30

Gln Arg Tyr
        35

<210> SEQ ID NO 245
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 245

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 246
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 246

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 247
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 247

Tyr Pro Ile Lys Pro Glu Ala Pro Gly Glu Asp Ala Ser Ala Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 248
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 248

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 249
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 249

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35
```

```
<210> SEQ ID NO 250
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 250

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 251

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 252
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 252

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 253
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

-continued

```
<220> FEATURE:
<221> NAME/KEY: MOD_RES
<222> LOCATION: (2)..(2)
<223> OTHER INFORMATION: homo-Lys

<400> SEQUENCE: 253

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 254

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 255
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 255

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 256
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 256

Pro Lys Pro Glu His Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 257
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 257

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 258
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 258

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 259
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 259

Ile Lys Pro Glu Ala Pro Gly Glu Asp Ala Ser Pro Glu Glu Leu Ala
1               5                   10                  15

Arg Tyr Tyr Ser Ala Leu Arg Ala Tyr Ile Asn Leu Ile Thr Arg Gln
            20                  25                  30

Arg Tyr

<210> SEQ ID NO 260
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 260

Tyr Pro Ile Lys Pro Glu Ala Pro Gly Glu Asp Ala Ser Pro Glu Glu
```

```
                1               5                   10                  15
Leu Ala Arg Tyr Tyr Ala Ser Leu Arg Ala Tyr Ile Asn Leu Ile Thr
                20                  25                  30
Arg Gln Arg Tyr
        35

<210> SEQ ID NO 261
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 261

Ile Lys Pro Glu Ala Pro Gly Glu Asp Ala Ser Pro Glu Glu Leu Ala
1               5                   10                  15
Arg Tyr Tyr Ala Ser Leu Arg Ala Tyr Ile Asn Leu Ile Thr Arg Gln
                20                  25                  30
Arg Tyr

<210> SEQ ID NO 262
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: homo-Lys

<400> SEQUENCE: 262

Pro Lys Pro Glu Ala Pro Gly Glu Asp Ala Ser Pro Glu Glu Leu Ala
1               5                   10                  15
Arg Tyr Tyr Ala Ser Leu Arg Ala Tyr Ile Asn Leu Ile Thr Arg Gln
                20                  25                  30
Arg Tyr

<210> SEQ ID NO 263
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 263

Pro Lys Pro Glu Ala Pro Gly Glu Asp Ala Ser Pro Glu Glu Leu Ala
1               5                   10                  15
Arg Tyr Tyr Ala Ser Leu Arg Ala Tyr Ile Asn Leu Ile Thr Arg Gln
                20                  25                  30
Arg Tyr

<210> SEQ ID NO 264
<211> LENGTH: 35
<212> TYPE: PRT
<213> ORGANISM: Artificial Sequence
<220> FEATURE:
```

<223> OTHER INFORMATION: Description of Artificial Sequence: Synthetic
peptide construct

<400> SEQUENCE: 264

Pro Pro Lys Pro Glu Ala Pro Gly Glu Asp Ala Ser Pro Glu Glu Leu
1               5                   10                  15

Ala Arg Tyr Tyr Ala Ser Leu Arg Ala Tyr Ile Asn Leu Ile Thr Arg
            20                  25                  30

Gln Arg Tyr
        35

<210> SEQ ID NO 265
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 265

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 266

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 267
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 267

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 268
<211> LENGTH: 36

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 268

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg Ala Tyr Ile Asn Leu Ile Thr
                20                  25                  30

Arg Gln Arg Tyr
        35

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 269

Ile Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
                20                  25                  30

Arg Tyr

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 270

Pro Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
                20                  25                  30

Arg Tyr

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: 8-amino-octanoyl-Ile

<400> SEQUENCE: 271

Ile Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
                20                  25                  30

Arg Tyr
```

```
<210> SEQ ID NO 272
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 272

Tyr Pro Ile Arg Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
                20                  25                  30

Arg Gln Arg Tyr
            35

<210> SEQ ID NO 273
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 273

Tyr Pro Ile Lys Pro Glu Ala Pro Gly Glu Asp Ala Pro Ala Glu Glu
1               5                   10                  15

Leu Ala Arg Tyr Tyr Ala Ser Leu Arg Ala Tyr Ile Asn Leu Ile Thr
                20                  25                  30

Arg Gln Arg Tyr
            35

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 274

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
                20                  25                  30

Arg Tyr

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 275

Pro Tyr Pro Ile Lys Pro Glu Ala Pro Gly Glu Asp Ala Pro Ala Glu
1               5                   10                  15

Glu Leu Ala Arg Tyr Tyr Ala Ser Leu Arg Ala Tyr Ile Asn Leu Ile
                20                  25                  30

Thr Arg Gln Arg Tyr
            35
```

```
<210> SEQ ID NO 276
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: 8-amino-octanoyl-Lys

<400> SEQUENCE: 276

Lys Pro Glu Ala Pro Gly Glu Asp Ala Pro Ala Glu Glu Leu Ala Arg
1               5                   10                  15

Tyr Tyr Ala Ser Leu Arg Ala Tyr Ile Asn Leu Ile Thr Arg Gln Arg
            20                  25                  30

Tyr

<210> SEQ ID NO 277
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 277

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 278
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 278

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 279
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 279

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
```

Arg Tyr

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Tyr

<400> SEQUENCE: 280

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
                20                  25                  30

Arg Gln Arg Tyr
            35

<210> SEQ ID NO 281
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile

<400> SEQUENCE: 281

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
                20                  25                  30

Arg Tyr

<210> SEQ ID NO 282
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Gly(Oct)

<400> SEQUENCE: 282

Gly Ile Lys Pro Glu Ala Pro Gly Glu Asp Ala Ser Pro Glu Glu Leu
1               5                   10                  15

Ala Arg Tyr Tyr Ser Ala Leu Arg His Tyr Ile Asn Leu Ile Thr Arg
                20                  25                  30

Gln Arg Tyr
        35

<210> SEQ ID NO 283
<211> LENGTH: 35
<212> TYPE: PRT

```
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Fmoc-Gly(Oct)

<400> SEQUENCE: 283

Gly Ile Lys Pro Glu Ala Pro Gly Glu Asp Ala Ser Pro Glu Leu
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Gly(Oct)

<400> SEQUENCE: 284

Gly Lys Pro Glu Ala Pro Gly Glu Asp Ala Ser Pro Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 285
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 285

Tyr Pro Ser Lys Pro Asp Asn Pro Gly Glu Asp Ala Pro Ala Glu Asp
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 286
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 286

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30
```

Arg Gln Arg Tyr
        35

<210> SEQ ID NO 287
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 287

Leu Glu Pro Val Tyr Pro Gly Asp Asn Ala Thr Pro Glu Gln Met Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 288
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 288

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Phe Leu Asn Leu Val Thr
            20                  25                  30

Arg Gln Arg Tyr
        35

<210> SEQ ID NO 289
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 289

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Pro
            20                  25                  30

Arg Gln Arg Tyr
        35

<210> SEQ ID NO 290
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (32)..(32)
<223> OTHER INFORMATION: Aib

<400> SEQUENCE: 290

Ala Pro Leu Glu Pro Val Tyr Pro Gly Asp Asn Ala Thr Pro Glu Gln

```
                1               5                  10                  15
Met Asn Arg Tyr Tyr Ala Ser Leu Arg His Tyr Leu Asn Leu Ala Xaa
                    20                  25                  30

Arg Gln Arg Tyr
            35

<210> SEQ ID NO 291
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (32)..(32)
<223> OTHER INFORMATION: Sar

<400> SEQUENCE: 291

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Xaa
                    20                  25                  30

Arg Gln Arg Tyr
            35

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 292

Ala Pro Leu Glu Pro Val Tyr Pro Gly Asp Asn Ala Thr Pro Glu Gln
1               5                   10                  15

Met Asn Arg Tyr Tyr Ser Ala Leu Arg His Tyr Leu Asn Leu Val Thr
                    20                  25                  30

Arg Gln Arg Tyr
            35

<210> SEQ ID NO 293
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 293

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
                    20                  25                  30

Arg Gln Arg Tyr
            35

<210> SEQ ID NO 294
<211> LENGTH: 36
<212> TYPE: PRT
<213> ORGANISM: Artificial Sequence
<220> FEATURE:
<223> OTHER INFORMATION: Description of Artificial Sequence: Synthetic
```

-continued peptide construct

<400> SEQUENCE: 294

Ala Pro Leu Glu Pro Val Tyr Pro Gly Asp Asn Ala Thr Pro Glu Gln
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 295
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 295

Ala Pro Leu Glu Pro Val Tyr Pro Gly Asp Asn Ala Thr Pro Glu Gln
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 296
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 296

Ala Pro Leu Glu Pro Val Tyr Pro Gly Asp Asn Ala Thr Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 297
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 297

Ala Pro Leu Glu Pro Val Tyr Pro Gly Asp Asn Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 298
<211> LENGTH: 36
<212> TYPE: PRT
<213> ORGANISM: Artificial Sequence
<220> FEATURE:

```
<223> OTHER INFORMATION: Description of Artificial Sequence: Synthetic
      peptide construct

<400> SEQUENCE: 298

Ala Pro Leu Glu Pro Val Tyr Pro Gly Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 299

Ala Pro Leu Glu Pro Val Tyr Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 300
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 300

Ala Pro Leu Glu Pro Val Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 301
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 301

Ala Pro Leu Glu Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 302
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      peptide construct

<400> SEQUENCE: 302

Ala Pro Leu Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 303
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ala

<400> SEQUENCE: 303

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
                20                  25                  30

Arg Gln Arg Tyr
            35

<210> SEQ ID NO 304
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)..(19)
<223> OTHER INFORMATION: homo-Arg

<400> SEQUENCE: 304

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
                20                  25                  30

Arg Gln Arg Tyr
            35

<210> SEQ ID NO 305
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ala
<220> FEATURE:
<221> NAME/KEY: MOD_RES
<222> LOCATION: (19)..(19)
<223> OTHER INFORMATION: homo-Arg
```

-continued

<400> SEQUENCE: 305

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 306
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)..(19)
<223> OTHER INFORMATION: homo-Lys

<400> SEQUENCE: 306

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
            20                  25                  30

Arg Gln Arg Tyr
        35

<210> SEQ ID NO 307
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 307

Ala Pro Met Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 308
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 308

Ala Pro Leu Glu Pro Val Tyr Pro Gly Asp Asn Ala Thr Pro Glu Gln
1               5                   10                  15

Met Asn Arg Tyr Tyr Ala Ser Leu Arg Ala Tyr Leu Asn Leu Val Thr
            20                  25                  30

Arg Gln Arg Tyr
        35

<210> SEQ ID NO 309
<211> LENGTH: 36

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 309

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Pro Arg Tyr
        35

<210> SEQ ID NO 310
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 310

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Pro
            20                  25                  30

Arg Tyr

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 311

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 312
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 312

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Gln
            20                  25                  30

Arg Tyr

<210> SEQ ID NO 313
<211> LENGTH: 36
<212> TYPE: PRT
```

-continued

```
<213> ORGANISM: Artificial Sequence
<220> FEATURE:
<223> OTHER INFORMATION: Description of Artificial Sequence: Synthetic
      peptide construct

<400> SEQUENCE: 313

Tyr Pro Ile Lys Pro Glu Ala Pro Gly Glu Asp Ala Ser Pro Glu Glu
1               5                   10                  15

Leu Ala Gln Tyr Ala Ala Ser Leu Arg His Tyr Ile Asn Met Leu Thr
                20                  25                  30

Arg Gln Arg Tyr
            35

<210> SEQ ID NO 314
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 314

Tyr Pro Ile Lys Pro Glu Ala Pro Gly Glu Asp Ala Ser Pro Glu Glu
1               5                   10                  15

Leu Ala Gln Tyr Ala Ser Ala Leu Arg His Tyr Ile Asn Met Leu Thr
                20                  25                  30

Arg Gln Arg Tyr
            35

<210> SEQ ID NO 315
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 315

Tyr Pro Ile Lys Pro Glu Ala Pro Gly Glu Asp Ala Ser Pro Glu Glu
1               5                   10                  15

Leu Ala Gln Tyr Ala Ala Asp Leu Arg His Tyr Ile Asn Met Leu Thr
                20                  25                  30

Arg Gln Arg Tyr
            35

<210> SEQ ID NO 316
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 316

Tyr Pro Ile Lys Pro Glu Ala Pro Gly Glu Asp Ala Ser Pro Glu Glu
1               5                   10                  15

Leu Asn Gln Tyr Ala Ala Asp Leu Arg Arg Tyr Ile Asn Met Leu Thr
                20                  25                  30

Arg Gln Arg Tyr
            35

<210> SEQ ID NO 317
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 317

Tyr Pro Ile Lys Pro Glu Ala Pro Gly Glu Asp Ala Ser Pro Glu Glu
1               5                   10                  15

Leu Asn Gln Tyr Ala Ala Ser Leu Arg Arg Tyr Ile Asn Met Leu Thr
            20                  25                  30

Arg Gln Arg Tyr
        35

<210> SEQ ID NO 318
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(2)
<223> OTHER INFORMATION: d-Ala

<400> SEQUENCE: 318

Tyr Ala Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 319
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 319

Ala Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 320
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Tyr

<400> SEQUENCE: 320

Tyr Pro Ile Lys Pro Glu Ala Pro Gly Glu Asp Ala Ser Pro Glu Glu
1               5                   10                  15
```

Leu Ala Gln Tyr Ala Ala Asp Leu Arg Arg Tyr Ile Asn Met Leu Thr
            20                  25                  30

Arg Gln Arg Tyr
        35

<210> SEQ ID NO 321
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(25)
<223> OTHER INFORMATION: homo-Lys

<400> SEQUENCE: 321

Tyr Pro Ile Lys Pro Glu Ala Pro Gly Glu Asp Ala Ser Pro Glu Glu
1               5                   10                  15

Leu Ala Gln Tyr Ala Ala Asp Leu Lys Arg Tyr Ile Asn Met Leu Thr
            20                  25                  30

Arg Gln Arg Tyr
        35

<210> SEQ ID NO 322
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(25)
<223> OTHER INFORMATION: homo-Arg

<400> SEQUENCE: 322

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 323
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(25)
<223> OTHER INFORMATION: Orn

<400> SEQUENCE: 323

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
            20                  25                  30

Arg Gln Arg Tyr
        35

```
<210> SEQ ID NO 324
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(25)
<223> OTHER INFORMATION: Cit

<400> SEQUENCE: 324

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
            20                  25                  30

Arg Gln Arg Tyr
        35

<210> SEQ ID NO 325
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)..(26)
<223> OTHER INFORMATION: homo-Lys

<400> SEQUENCE: 325

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Lys Tyr Ile Asn Met Leu Thr
            20                  25                  30

Arg Gln Arg Tyr
        35

<210> SEQ ID NO 326
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)..(26)
<223> OTHER INFORMATION: homo-Arg

<400> SEQUENCE: 326

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 327
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (26)..(26)
<223> OTHER INFORMATION: Orn

<400> SEQUENCE: 327

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 328
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)..(26)
<223> OTHER INFORMATION: Cit

<400> SEQUENCE: 328

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 329
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(26)
<223> OTHER INFORMATION: homo-Arg

<400> SEQUENCE: 329

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 330
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 330
```

```
Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 331
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Tyr
<220> FEATURE:
<221> NAME/KEY: MOD_RES
<222> LOCATION: (4)..(4)
<223> OTHER INFORMATION: homo-Lys

<400> SEQUENCE: 331

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 332
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Arg

<400> SEQUENCE: 332

Tyr Pro Ile Arg Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)..(8)
<223> OTHER INFORMATION: homo-Pro

<400> SEQUENCE: 333

Tyr Pro Ile Lys Pro Glu Ala Pro Gly Glu Asp Ala Ser Pro Glu Glu
1               5                   10                  15
```

Leu Ala Gln Tyr Ala Ala Asp Leu Arg Arg Tyr Ile Asn Met Leu Thr
            20                  25                  30

Arg Gln Arg Tyr
        35

<210> SEQ ID NO 334
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)..(8)
<223> OTHER INFORMATION: Aib

<400> SEQUENCE: 334

Tyr Pro Ile Lys Pro Glu Ala Xaa Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 335
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 335

Tyr Pro Ile Lys Pro Glu Ala Gly Pro Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)..(14)
<223> OTHER INFORMATION: homo-Pro

<400> SEQUENCE: 336

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 337
<211> LENGTH: 36
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)..(14)
<223> OTHER INFORMATION: Aib

<400> SEQUENCE: 337

Tyr Pro Ile Lys Pro Glu Ala Pro Gly Glu Asp Ala Ser Xaa Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 338
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)..(9)
<223> OTHER INFORMATION: Sar

<400> SEQUENCE: 338

Tyr Pro Ile Lys Pro Glu Ala Pro Xaa Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 339
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)..(13)
<223> OTHER INFORMATION: homo-Ser

<400> SEQUENCE: 339

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 340
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)..(13)
<223> OTHER INFORMATION: Dap
```

```
<400> SEQUENCE: 340

Tyr Pro Ile Lys Pro Glu Ala Pro Gly Glu Asp Ala Xaa Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 341

Tyr Pro Ile Lys Pro Glu Ala Pro Gly Glu Asp Ala Ser Pro Gln Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 342
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 342

Tyr Pro Ile Lys Pro Glu Ala Pro Gly Glu Asp Ala Ser Pro Asp Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 343

Tyr Pro Ile Lys Pro Glu Ala Pro Gly Glu Asp Ala Ser Pro Glu Glu
1               5                   10                  15

Met Ala Gln Tyr Ala Ala Asp Leu Arg Arg Tyr Ile Asn Met Leu Thr
            20                  25                  30

Arg Gln Arg Tyr
        35

<210> SEQ ID NO 344
<211> LENGTH: 36
<212> TYPE: PRT
<213> ORGANISM: Artificial Sequence
<220> FEATURE:
<223> OTHER INFORMATION: Description of Artificial Sequence: Synthetic
```

```
                        peptide construct
<220> FEATURE:
<221> NAME/KEY: MOD_RES
<222> LOCATION: (4)..(4)
<223> OTHER INFORMATION: homo-Lys

<400> SEQUENCE: 344

Tyr Pro Ile Lys Pro Glu Ala Pro Gly Glu Asp Ala Ser Ala Gln Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 345

Tyr Pro Ile Lys Pro Glu Ala Pro Gly Glu Asp Ala Ser Ala Ser Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 346
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)..(4)
<223> OTHER INFORMATION: homo-Lys

<400> SEQUENCE: 346

Tyr Pro Ile Lys Pro Glu Ala Pro Gly Glu Asp Ala Ser Ala Gln Glu
1               5                   10                  15

Met Ala Gln Tyr Ala Ala Asp Leu Arg Arg Tyr Ile Asn Met Leu Thr
            20                  25                  30

Arg Gln Arg Tyr
        35

<210> SEQ ID NO 347
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 347

Tyr Pro Ile Lys Pro Glu Ala Pro Gly Glu Asp Ala Ser Pro Glu Glu
1               5                   10                  15
```

Leu Ala Gln Tyr Ala Ala Glu Leu Arg Arg Tyr Ile Gln Met Leu Thr
            20                  25                  30

Arg Gln Arg Tyr
        35

<210> SEQ ID NO 348
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Tyr, Phe, Trp, or absent
<220> FEATURE:
<221> NAME/KEY: MOD_RES
<222> LOCATION: (2)..(2)
<223> OTHER INFORMATION: Pro, Gly, d-Ala, homo-Pro, hyroxy-Pro, or
      absent
<220> FEATURE:
<221> NAME/KEY: MOD_RES
<222> LOCATION: (3)..(3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)..(4)
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)..(6)
<223> OTHER INFORMATION: Glu, Ala, Val, Asp, Asn, or Gln
<220> FEATURE:
<221> NAME/KEY: MOD_RES
<222> LOCATION: (7)..(7)
<223> OTHER INFORMATION: Ala, Asn, His, Ser, or Tyr
<220> FEATURE:
<221> NAME/KEY: MOD_RES
<222> LOCATION: (9)..(9)
<223> OTHER INFORMATION: Gly, Ala, Ser, Sarcosine, Pro, or Aib
<220> FEATURE:
<221> NAME/KEY: MOD_RES
<222> LOCATION: (10)..(10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)..(11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)..(12)
<223> OTHER INFORMATION: Ala or d-Ala
<220> FEATURE:
<221> NAME/KEY: MOD_RES
<222> LOCATION: (13)..(13)
<223> OTHER INFORMATION: Ser, Ala, Thr, Pro, or homo-Ser
<220> FEATURE:
<221> NAME/KEY: MOD_RES
<222> LOCATION: (14)..(14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)..(15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)..(16)
<223> OTHER INFORMATION: Glu, Ala, Asp, Asn, or Gln
<220> FEATURE:
<221> NAME/KEY: MOD_RES
<222> LOCATION: (17)..(17)
<223> OTHER INFORMATION: Leu, Ala, Met, Trp, Ile, Val, or NorVal
<220> FEATURE:
<221> NAME/KEY: MOD_RES
<222> LOCATION: (18)..(18)

```
<223> OTHER INFORMATION: Asn, Asp, Ala, Glu, Gln, Ser, or Thr
<220> FEATURE:
<221> NAME/KEY: MOD_RES
<222> LOCATION: (19)..(19)
<223> OTHER INFORMATION: Arg, Tyr, Lys, Ala, Gln, or N(Me)Ala
<220> FEATURE:
<221> NAME/KEY: MOD_RES
<222> LOCATION: (21)..(21)
<223> OTHER INFORMATION: Tyr, Ala, Met, Phe, or Leu
<220> FEATURE:
<221> NAME/KEY: MOD_RES
<222> LOCATION: (22)..(22)
<223> OTHER INFORMATION: Ala, Ser, Thr, or d-Ala
<220> FEATURE:
<221> NAME/KEY: MOD_RES
<222> LOCATION: (23)..(23)
<223> OTHER INFORMATION: Ser, Ala, Thr, or homo-Ser
<220> FEATURE:
<221> NAME/KEY: MOD_RES
<222> LOCATION: (26)..(26)
<223> OTHER INFORMATION: His or Ala
<220> FEATURE:
<221> NAME/KEY: MOD_RES
<222> LOCATION: (28)..(28)
<223> OTHER INFORMATION: Leu, Ile, Val, or Ala
<220> FEATURE:
<221> NAME/KEY: MOD_RES
<222> LOCATION: (30)..(30)
<223> OTHER INFORMATION: Leu, Ala, NorVal, Val, Ile, or Met
<220> FEATURE:
<221> NAME/KEY: MOD_RES
<222> LOCATION: (31)..(31)
<223> OTHER INFORMATION: Ala, Val, Ile, or Leu
<220> FEATURE:
<221> NAME/KEY: MOD_RES
<222> LOCATION: (36)..(36)
<223> OTHER INFORMATION: Tyr, N(Me)Tyr, His, Trp, or Phe

<400> SEQUENCE: 348

Xaa Xaa Xaa Xaa Pro Xaa Xaa Pro Xaa Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 349
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Tyr, Phe, Trp, or absent
<220> FEATURE:
<221> NAME/KEY: MOD_RES
<222> LOCATION: (2)..(2)
<223> OTHER INFORMATION: Pro, Gly, d-Ala, homo-Pro, hydroxy-Pro, or
      absent
<220> FEATURE:
<221> NAME/KEY: MOD_RES
<222> LOCATION: (3)..(3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)..(4)
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)..(6)
<223> OTHER INFORMATION: Glu, Ala, Val, Asp, Asn, or Gln
```

```
<220> FEATURE:
<221> NAME/KEY: MOD_RES
<222> LOCATION: (7)..(7)
<223> OTHER INFORMATION: Ala, Asn, His, Ser, or Tyr
<220> FEATURE:
<221> NAME/KEY: MOD_RES
<222> LOCATION: (9)..(9)
<223> OTHER INFORMATION: Gly, Ala, Ser, Sarcosine, Pro, or Aib
<220> FEATURE:
<221> NAME/KEY: MOD_RES
<222> LOCATION: (10)..(10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)..(11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)..(12)
<223> OTHER INFORMATION: Ala or d-Ala
<220> FEATURE:
<221> NAME/KEY: MOD_RES
<222> LOCATION: (13)..(13)
<223> OTHER INFORMATION: Ser, Ala, Thr, or homo-Ser
<220> FEATURE:
<221> NAME/KEY: MOD_RES
<222> LOCATION: (14)..(14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)..(15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)..(16)
<223> OTHER INFORMATION: Glu, Ala, Asp, Asn, or Gln
<220> FEATURE:
<221> NAME/KEY: MOD_RES
<222> LOCATION: (17)..(17)
<223> OTHER INFORMATION: Leu, Ala, Met, Trp, Ile, Val, or NorVal
<220> FEATURE:
<221> NAME/KEY: MOD_RES
<222> LOCATION: (18)..(18)
<223> OTHER INFORMATION: Asn, Asp, Ala, Glu, Gln, Ser, or Thr
<220> FEATURE:
<221> NAME/KEY: MOD_RES
<222> LOCATION: (19)..(19)
<223> OTHER INFORMATION: Arg, Tyr, Lys, Ala, Gln, or N(Me)Ala
<220> FEATURE:
<221> NAME/KEY: MOD_RES
<222> LOCATION: (21)..(21)
<223> OTHER INFORMATION: Tyr, Ala, Met, Phe, or Leu
<220> FEATURE:
<221> NAME/KEY: MOD_RES
<222> LOCATION: (22)..(22)
<223> OTHER INFORMATION: Ala, Ser, Thr, or d-Ala
<220> FEATURE:
<221> NAME/KEY: MOD_RES
<222> LOCATION: (23)..(23)
<223> OTHER INFORMATION: Ser, Ala, Thr, or homo-Ser
<220> FEATURE:
<221> NAME/KEY: MOD_RES
<222> LOCATION: (26)..(26)
<223> OTHER INFORMATION: His or Ala
<220> FEATURE:
<221> NAME/KEY: MOD_RES
<222> LOCATION: (28)..(28)
<223> OTHER INFORMATION: Leu, Ile, Val, or Ala
<220> FEATURE:
<221> NAME/KEY: MOD_RES
<222> LOCATION: (30)..(30)
<223> OTHER INFORMATION: Leu, Ala, NorVal, Val, Ile, or Met
<220> FEATURE:
<221> NAME/KEY: MOD_RES
<222> LOCATION: (31)..(31)
<223> OTHER INFORMATION: Ala, Val, Ile, or Leu
<220> FEATURE:
<221> NAME/KEY: MOD_RES
<222> LOCATION: (36)..(36)
```

<223> OTHER INFORMATION: Tyr, N(Me)Tyr, His, Trp, or Phe

<400> SEQUENCE: 349

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 350
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Ile, Ala, Pro, Ser, Thr, or NorVal
<220> FEATURE:
<221> NAME/KEY: MOD_RES
<222> LOCATION: (2)..(2)
<223> OTHER INFORMATION: Lys, Ala, Gly, Glu, Asp, d-Ala, homo-Lys, or
      homo-Arg
<220> FEATURE:
<221> NAME/KEY: MOD_RES
<222> LOCATION: (4)..(4)
<223> OTHER INFORMATION: Glu, Ala, Val, Asp, Asn, or Gln
<220> FEATURE:
<221> NAME/KEY: MOD_RES
<222> LOCATION: (5)..(5)
<223> OTHER INFORMATION: Ala, Asn, His, Ser, or Tyr
<220> FEATURE:
<221> NAME/KEY: MOD_RES
<222> LOCATION: (7)..(7)
<223> OTHER INFORMATION: Gly, Ala, Ser, Sarcosine, Pro, or Aib
<220> FEATURE:
<221> NAME/KEY: MOD_RES
<222> LOCATION: (8)..(8)
<223> OTHER INFORMATION: Glu, Ala, Asp, Asn, Gln, Pro, Aib, or Gly
<220> FEATURE:
<221> NAME/KEY: MOD_RES
<222> LOCATION: (9)..(9)
<223> OTHER INFORMATION: Asp, Ala, Glu, Asn, Gln, Pro, Aib, or Gly
<220> FEATURE:
<221> NAME/KEY: MOD_RES
<222> LOCATION: (10)..(10)
<223> OTHER INFORMATION: Ala or d-Ala
<220> FEATURE:
<221> NAME/KEY: MOD_RES
<222> LOCATION: (11)..(11)
<223> OTHER INFORMATION: Ser, Ala, Thr, or homo-Ser
<220> FEATURE:
<221> NAME/KEY: MOD_RES
<222> LOCATION: (12)..(12)
<223> OTHER INFORMATION: Pro, Ala, homo-Pro, hydroxy-Pro, Aib, or Gly
<220> FEATURE:
<221> NAME/KEY: MOD_RES
<222> LOCATION: (13)..(13)
<223> OTHER INFORMATION: Glu, Ala, Asp, Asn, Gln, Pro, Aib, or Gly
<220> FEATURE:
<221> NAME/KEY: MOD_RES
<222> LOCATION: (14)..(14)
<223> OTHER INFORMATION: Glu, Ala, Asp, Asn, or Gln
<220> FEATURE:
<221> NAME/KEY: MOD_RES
<222> LOCATION: (15)..(15)
<223> OTHER INFORMATION: Leu, Ala, Met, Trp, Ile, Val, or NorVal
<220> FEATURE:
<221> NAME/KEY: MOD_RES
<222> LOCATION: (16)..(16)
<223> OTHER INFORMATION: Asn, Asp, Ala, Glu, Gln, Ser or Thr
<220> FEATURE:

```
<221> NAME/KEY: MOD_RES
<222> LOCATION: (17)..(17)
<223> OTHER INFORMATION: Arg, Tyr, Lys, Ala, Gln, or N(Me)Ala
<220> FEATURE:
<221> NAME/KEY: MOD_RES
<222> LOCATION: (19)..(19)
<223> OTHER INFORMATION: Tyr, Ala, Met, Phe, or Leu
<220> FEATURE:
<221> NAME/KEY: MOD_RES
<222> LOCATION: (20)..(20)
<223> OTHER INFORMATION: Ala, Ser, Thr, or d-Ala
<220> FEATURE:
<221> NAME/KEY: MOD_RES
<222> LOCATION: (21)..(21)
<223> OTHER INFORMATION: Ser, Ala, Thr, or homo-Ser
<220> FEATURE:
<221> NAME/KEY: MOD_RES
<222> LOCATION: (24)..(24)
<223> OTHER INFORMATION: His or Ala
<220> FEATURE:
<221> NAME/KEY: MOD_RES
<222> LOCATION: (26)..(26)
<223> OTHER INFORMATION: Leu or Ala
<220> FEATURE:
<221> NAME/KEY: MOD_RES
<222> LOCATION: (28)..(28)
<223> OTHER INFORMATION: Leu, Ala, NorVal, or Ile
<220> FEATURE:
<221> NAME/KEY: MOD_RES
<222> LOCATION: (29)..(29)
<223> OTHER INFORMATION: Ala or Val
<220> FEATURE:
<221> NAME/KEY: MOD_RES
<222> LOCATION: (34)..(34)
<223> OTHER INFORMATION: Tyr, N(Me)Tyr, His, or Trp

<400> SEQUENCE: 350

Xaa Xaa Pro Xaa Xaa Pro Xaa Xaa Xaa Xaa Xaa Xaa Xaa Xaa Xaa
1               5                   10                  15

Xaa Tyr Xaa Xaa Xaa Leu Arg Xaa Tyr Xaa Asn Xaa Xaa Thr Arg Gln
            20                  25                  30

Arg Xaa

<210> SEQ ID NO 351
<211> LENGTH: 4
<212> TYPE: PRT
<213> ORGANISM: Homo sapiens

<400> SEQUENCE: 351

Thr Arg Gln Arg
1

<210> SEQ ID NO 352
<211> LENGTH: 27
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 211

<400> SEQUENCE: 352

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 353
<211> LENGTH: 26
<212> TYPE: PRT
<213> ORGANISM: Artificial Sequence
```

```
<220> FEATURE:
<223> OTHER INFORMATION: Description of Artificial Sequence: N-term
      Mimic A linker to SEQ ID NO: 212

<400> SEQUENCE: 353

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 354
<211> LENGTH: 25
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 213

<400> SEQUENCE: 354

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 355
<211> LENGTH: 24
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 214

<400> SEQUENCE: 355

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 356
<211> LENGTH: 23
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 215

<400> SEQUENCE: 356

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 357
<211> LENGTH: 22
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 216

<400> SEQUENCE: 357

Glu Glu Leu Asn Arg Tyr Tyr Ala Ser Leu Arg His Tyr Leu Asn Leu
1               5                   10                  15

Val Thr Arg Gln Arg Tyr
            20
```

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: N-term
      Mimic A linker to SEQ ID NO: 217

<400> SEQUENCE: 358

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 359
<211> LENGTH: 27
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 231

<400> SEQUENCE: 359

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 360
<211> LENGTH: 26
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 232

<400> SEQUENCE: 360

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 361
<211> LENGTH: 25
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 233

<400> SEQUENCE: 361

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 362
<211> LENGTH: 24
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 234

<400> SEQUENCE: 362

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 363
<211> LENGTH: 23
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 235

<400> SEQUENCE: 363

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 364
<211> LENGTH: 22
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 236

<400> SEQUENCE: 364

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: N-term
      Mimic B linker to SEQ ID NO: 237

<400> SEQUENCE: 365

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 366
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 366

Pro Ser Lys Pro Asp Asn Pro Gly Glu Asp Ala Pro Ala Glu Asp Met
1               5                   10                  15

Ala Arg Tyr Tyr Ser Ala Leu Arg His Tyr Ile Asn Leu Ile Thr Arg
                20                  25                  30

Gln Arg Tyr
        35

```
<210> SEQ ID NO 367
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 367

Lys Pro Asp Asn Pro Gly Glu Asp Ala Pro Ala Glu Asp Met Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 368
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 368

Pro Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 369
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 369

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 370
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 370

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Met Leu Thr Arg
            20                  25                  30

Pro Arg Tyr
        35

<210> SEQ ID NO 371
```

<211> LENGTH: 33
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 371

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
            20                  25                  30

Tyr

<210> SEQ ID NO 372
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 372

Ala Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 373
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 373

Tyr Pro Ala Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 374
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 374

Tyr Pro Ser Ala Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 375

<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 375

Tyr Pro Ser Lys Pro Ala Asn Pro Gly Glu Asp Ala Pro Ala Glu Asp
1               5                   10                  15
Met Ala Arg Tyr Tyr Ser Ala Leu Arg His Tyr Ile Asn Leu Ile Thr
            20                  25                  30
Arg Gln Arg Tyr
        35

<210> SEQ ID NO 376
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 376

Tyr Pro Ser Lys Pro Asp Ala Pro Gly Glu Asp Ala Pro Ala Glu Asp
1               5                   10                  15
Met Ala Arg Tyr Tyr Ser Ala Leu Arg His Tyr Ile Asn Leu Ile Thr
            20                  25                  30
Arg Gln Arg Tyr
        35

<210> SEQ ID NO 377
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 377

Tyr Pro Ser Lys Pro Lys Tyr Pro Gly Glu Asp Ala Pro Ala Glu Asp
1               5                   10                  15
Leu Ala Arg Tyr Tyr Ser Ala Leu Arg His Tyr Ile Asn Leu Ile Thr
            20                  25                  30
Arg Gln Arg Tyr
        35

<210> SEQ ID NO 378
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 378

Tyr Pro Ser Lys Pro Asp Asn Pro Ala Glu Asp Ala Pro Ala Glu Asp
1               5                   10                  15
Met Ala Arg Tyr Tyr Ser Ala Leu Arg His Tyr Ile Asn Leu Ile Thr
            20                  25                  30
Arg Gln Arg Tyr
        35

```
<210> SEQ ID NO 379
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 379

Tyr Pro Ser Lys Pro Asp Asn Pro Gly Ala Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 380
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 380

Tyr Pro Ser Lys Pro Asp Asn Pro Gly Glu Ala Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 381
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 381

Tyr Pro Ser Lys Pro Asp Asn Pro Gly Glu Asp Ala Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 382
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 382

Tyr Pro Ser Lys Pro Asp Asn Pro Gly Glu Asp Ala Pro Gly Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35
```

<210> SEQ ID NO 383
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 383

Tyr Pro Ser Lys Pro Asp Asn Pro Gly Glu Asp Ala Pro Ala Ala Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 384
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 384

Tyr Pro Ser Lys Pro Asp Asn Pro Gly Glu Asp Ala Pro Ala Glu Ala
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 385
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 385

Tyr Pro Ser Lys Pro Asp Asn Pro Gly Glu Asp Ala Pro Ala Glu Asp
1               5                   10                  15

Ala Ala Arg Tyr Tyr Ser Ala Leu Arg His Tyr Ile Asn Leu Ile Thr
            20                  25                  30

Arg Gln Arg Tyr
        35

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 386

Tyr Pro Ser Lys Pro Asp Asn Pro Gly Glu Asp Ala Pro Ala Glu Asp
1               5                   10                  15

Met Ala Ala Tyr Tyr Ser Ala Leu Arg His Tyr Ile Asn Leu Ile Thr
            20                  25                  30

Arg Gln Arg Tyr
        35

<210> SEQ ID NO 387
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 387

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Ile Thr
            20                  25                  30

Arg Gln Arg Tyr
        35

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 388

Tyr Pro Ser Lys Pro Asp Asn Pro Gly Glu Asp Ala Pro Ala Glu Asp
1               5                   10                  15

Met Ala Arg Tyr Ala Ser Ala Leu Arg His Tyr Ile Asn Leu Ile Thr
            20                  25                  30

Arg Gln Arg Tyr
        35

<210> SEQ ID NO 389
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 389

Tyr Pro Ser Lys Pro Asp Asn Pro Gly Glu Asp Ala Pro Ala Glu Asp
1               5                   10                  15

Met Ala Arg Tyr Tyr Ala Ala Leu Arg His Tyr Ile Asn Leu Ile Thr
            20                  25                  30

Arg Gln Arg Tyr
        35

<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 390

Tyr Pro Ser Lys Pro Asp Asn Pro Gly Glu Asp Ala Pro Ala Glu Asp
1               5                   10                  15

Met Ala Arg Tyr Tyr Ser Ala Leu Lys His Tyr Ile Asn Leu Ile Thr
            20                  25                  30

Arg Gln Arg Tyr

<210> SEQ ID NO 391
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 391

Tyr Pro Ser Lys Pro Asp Asn Pro Gly Glu Asp Ala Pro Ala Glu Asp
1               5                   10                  15

Met Ala Arg Tyr Tyr Ser Ala Leu Arg Ala Tyr Ile Asn Leu Ile Thr
            20                  25                  30

Arg Gln Arg Tyr
        35

<210> SEQ ID NO 392
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 392

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Phe Ile Asn Leu Ile Thr
            20                  25                  30

Arg Gln Arg Tyr
        35

<210> SEQ ID NO 393
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 393

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ala Asn Leu Ile Thr
            20                  25                  30

Arg Gln Arg Tyr
        35

<210> SEQ ID NO 394
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 394

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Gln Leu Ile Thr
            20                  25                  30

Arg Gln Arg Tyr
        35

<210> SEQ ID NO 395
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 395

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Ala Ile Thr
            20                  25                  30

Arg Gln Arg Tyr
        35

<210> SEQ ID NO 396
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 396

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 397
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 397

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Phe
        35

<210> SEQ ID NO 398
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 398

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg His
        35

<210> SEQ ID NO 399
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 399

Leu Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 400
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 400

Val Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 401
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 401

Tyr Pro Ile Lys Pro Glu Ala Pro Gly Glu Asp Ala Pro Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 402
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 402

Ala Pro Leu Glu Pro Val Tyr Pro Ser Lys Pro Lys Asn Pro Gly
1               5                   10                  15

Glu Asp Ala Pro Ala Glu Asp Leu Ala Arg Tyr Tyr Ser Ala Leu Arg
            20                  25                  30

His Tyr Ile Asn Leu Ile Thr Arg Gln Arg Tyr
        35                  40

<210> SEQ ID NO 403
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 403

Ala Pro Leu Glu Pro Val Tyr Pro Gly Asp Asn Ala Thr Pro Glu Gln
1               5                   10                  15

Met Tyr Pro Ser Lys Pro Lys Asn Pro Gly Glu Asp Ala Pro Ala Glu
                20                  25                  30

Asp Leu Ala Arg Tyr Tyr Ser Ala Leu Arg His Tyr Ile Asn Leu Ile
                35                  40                  45

Thr Arg Gln Arg Tyr
        50

<210> SEQ ID NO 404
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 404

Gln Tyr Ala Ala Asp Tyr Pro Ser Lys Pro Lys Asn Pro Gly Glu Asp
1               5                   10                  15

Ala Pro Ala Glu Asp Leu Ala Arg Tyr Tyr Ser Ala Leu Arg His Tyr
                20                  25                  30

Ile Asn Leu Ile Thr Arg Gln Arg Tyr
        35                  40

<210> SEQ ID NO 405
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 405

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Val Thr Arg Gln
                20                  25                  30

Arg Tyr

<210> SEQ ID NO 406
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 406

Ile Lys Pro Glu Ala Pro Gly Glu Asp Ala Ser Pro Glu Glu Leu Asn
1               5                   10                  15

```
Arg Tyr Tyr Ala Ser Leu Arg His Tyr Ile Asn Leu Val Thr Arg Gln
            20                  25                  30

Arg Tyr

<210> SEQ ID NO 407
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 407

Ile Lys Pro Glu Ala Pro Gly Glu Asp Ala Ser Pro Glu Glu Leu Asn
1               5                   10                  15

Arg Tyr Tyr Ala Ser Leu Arg His Tyr Val Asn Leu Val Thr Arg Gln
            20                  25                  30

Arg Tyr

<210> SEQ ID NO 408
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 408

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Val Thr Arg Gln
            20                  25                  30

Arg Tyr

<210> SEQ ID NO 409
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 409

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Tyr

<210> SEQ ID NO 410
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 410

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ile Thr Arg Gln
            20                  25                  30
```

Arg Tyr

<210> SEQ ID NO 411
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 411

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 412
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 412

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Phe

<210> SEQ ID NO 413
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 413

Ile Lys Pro Glu Ala Pro Gly Glu Asp Ala Ser Pro Glu Glu Leu Asn
1               5                   10                  15

Arg Tyr Tyr Ala Ser Leu Lys His Phe Leu Asn Leu Val Thr Arg Gln
            20                  25                  30

Arg Tyr

<210> SEQ ID NO 414
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 414

Ile Lys Pro Glu Ala Pro Gly Glu Asp Ala Ser Pro Glu Glu Leu Asn
1               5                   10                  15

Arg Tyr Tyr Ala Ser Leu Lys His Tyr Ile Asn Leu Val Thr Arg Gln
            20                  25                  30

Arg Tyr

-continued

```
<210> SEQ ID NO 415
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 415

Ile Lys Pro Glu Ala Pro Gly Glu Asp Ala Ser Pro Glu Glu Leu Asn
1               5                   10                  15

Arg Tyr Tyr Ala Ser Leu Lys His Tyr Val Asn Leu Val Thr Arg Gln
            20                  25                  30

Arg Tyr

<210> SEQ ID NO 416
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 416

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Gln Leu Val Thr Arg Gln
            20                  25                  30

Arg Tyr

<210> SEQ ID NO 417
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 417

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Val Val Thr Arg Gln
            20                  25                  30

Arg Tyr

<210> SEQ ID NO 418
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 418

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Ile Thr Arg Gln
            20                  25                  30

Arg Tyr

<210> SEQ ID NO 419
<211> LENGTH: 34
<212> TYPE: PRT
```

<213> ORGANISM: Artificial Sequence
<220> FEATURE:
<223> OTHER INFORMATION: Description of Artificial Sequence: Synthetic
      peptide construct

<400> SEQUENCE: 419

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Leu Thr Arg Gln
            20                  25                  30

Arg Tyr

<210> SEQ ID NO 420
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 420

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Phe

<210> SEQ ID NO 421
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 421

Ile Lys Pro Glu Ala Pro Gly Glu Asp Ala Ser Pro Glu Glu Leu Asn
1               5                   10                  15

Arg Tyr Tyr Ala Ser Leu Arg His Phe Ile Asn Leu Val Thr Arg Gln
            20                  25                  30

Arg Tyr

<210> SEQ ID NO 422
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 422

Ile Lys Pro Glu Ala Pro Gly Glu Asp Ala Ser Pro Glu Glu Leu Asn
1               5                   10                  15

Arg Tyr Tyr Ala Ser Leu Arg His Phe Val Asn Leu Val Thr Arg Gln
            20                  25                  30

Arg Tyr

<210> SEQ ID NO 423
<211> LENGTH: 34
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 423

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Gln Leu Val Thr Arg Gln
            20                  25                  30

Arg Tyr

<210> SEQ ID NO 424
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 424

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Val Val Thr Arg Gln
            20                  25                  30

Arg Tyr

<210> SEQ ID NO 425
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 425

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Ile Thr Arg Gln
            20                  25                  30

Arg Tyr

<210> SEQ ID NO 426
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 426

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Leu Thr Arg Gln
            20                  25                  30

Arg Tyr

<210> SEQ ID NO 427
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 427

-continued

```
Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Val Thr Arg Gln
            20                  25                  30

Arg Phe

<210> SEQ ID NO 428
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 428

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Val Val Thr Arg Gln
            20                  25                  30

Arg Tyr

<210> SEQ ID NO 429
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 429

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Ile Thr Arg Gln
            20                  25                  30

Arg Tyr

<210> SEQ ID NO 430
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 430

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Leu Thr Arg Gln
            20                  25                  30

Arg Tyr

<210> SEQ ID NO 431
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 431

Ile Lys Pro Glu Ala Pro Gly Glu Asp Ala Ser Pro Glu Glu Leu Asn
1               5                   10                  15
```

Arg Tyr Tyr Ala Ser Leu Arg His Tyr Leu Gln Leu Val Thr Arg Gln
            20                  25                  30

Arg Phe

<210> SEQ ID NO 432
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 432

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Ile Thr Arg Gln
            20                  25                  30

Arg Tyr

<210> SEQ ID NO 433
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 433

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Leu Thr Arg Gln
            20                  25                  30

Arg Tyr

<210> SEQ ID NO 434
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 434

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Phe

<210> SEQ ID NO 435
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 435

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Phe

<210> SEQ ID NO 436
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 436

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 437
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 437

Pro Lys Pro Glu His Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 438
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 438

Pro Lys Pro Glu His Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 439
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 439

Pro Lys Pro Glu His Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln

-continued

```
                20                  25                  30
Arg Tyr

<210> SEQ ID NO 440
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 440

Pro Lys Pro Glu Ala Pro Gly Glu Asp Ala Ser Pro Glu Glu Leu Ala
1               5                   10                  15

Lys Tyr Tyr Ala Ser Leu Arg Ala Tyr Ile Asn Leu Ile Thr Arg Gln
                20                  25                  30

Arg Tyr

<210> SEQ ID NO 441
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 441

Pro Lys Pro Glu Ala Pro Gly Glu Asp Ala Ser Pro Glu Glu Leu Ala
1               5                   10                  15

Lys Tyr Tyr Ala Ser Leu Arg Ala Tyr Ile Asn Leu Ile Thr Arg Gln
                20                  25                  30

Arg Tyr

<210> SEQ ID NO 442
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 442

Pro Lys Pro Glu His Pro Gly Glu Asp Ala Pro Ala Glu Glu Leu Ala
1               5                   10                  15

Lys Tyr Tyr Ala Ser Leu Arg Ala Tyr Ile Asn Leu Ile Thr Arg Gln
                20                  25                  30

Arg Tyr

<210> SEQ ID NO 443
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 443

Ile Lys Pro Glu Ala Pro Gly Glu Asp Ala Ser Pro Glu Glu Leu Asn
1               5                   10                  15
```

Arg Tyr Tyr Ala Ser Leu Arg His Tyr Leu Asn Leu Val Thr Arg Gln
            20                  25                  30

Lys Tyr

<210> SEQ ID NO 444
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isobutyloxycarbonyl-Pro

<400> SEQUENCE: 444

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 445
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 445

Pro Lys Pro Glu His Pro Gly Glu Asp Ala Ser Pro Glu Glu Leu Asn
1               5                   10                  15

Arg Tyr Tyr Ala Ser Leu Arg Ala Tyr Ile Asn Leu Val Thr Arg Gln
            20                  25                  30

Arg Tyr

<210> SEQ ID NO 446
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 446

Pro Lys Pro Glu Ala Pro Gly Glu Asp Ala Ser Pro Glu Glu Ile Asn
1               5                   10                  15

Arg Tyr Phe Ala Ser Leu Arg Ala Tyr Ile Asn Leu Val Thr Arg Gln
            20                  25                  30

Arg Tyr

<210> SEQ ID NO 447
<211> LENGTH: 34
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 447

Pro Lys Pro Glu Ala Pro Gly Glu Asp Ala Ser Pro Glu Glu Leu Asn
1               5                   10                  15

Arg Tyr Lys Ala Ser Leu Arg Ala Tyr Leu Asn Leu Val Thr Arg Gln
            20                  25                  30

Arg Tyr

<210> SEQ ID NO 448
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 448

Pro Lys Pro Glu Ala Pro Gly Glu Asp Ala Ser Pro Glu Glu Ile Asn
1               5                   10                  15

Arg Tyr Phe Ala Ser Leu Arg Ala Tyr Ile Asn Leu Val Thr Arg Gln
            20                  25                  30

Arg Tyr

<210> SEQ ID NO 449
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 449

Pro Lys Pro Glu Ala Pro Gly Glu Asp Ala Ser Pro Glu Glu Leu Asn
1               5                   10                  15

Arg Tyr Lys Ala Ser Leu Arg Ala Tyr Leu Asn Leu Val Thr Arg Gln
            20                  25                  30

Arg Tyr

<210> SEQ ID NO 450
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 450

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Trp

<210> SEQ ID NO 451
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: (NMe)Ala

<400> SEQUENCE: 451

Pro Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 452
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Dansyl-Ile

<400> SEQUENCE: 452

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 453
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 453

Ile Lys Ala Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 454
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 454

Pro Lys Pro Glu Ala Pro Gly Glu Asp Ala Ser Pro Glu Asp Leu Ala
1               5                   10                  15
```

Arg Tyr Lys Ala Ser Leu Arg Ala Tyr Ile Asn Leu Ile Thr Arg Gln
            20                  25                  30

Arg Tyr

<210> SEQ ID NO 455
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Octanoyl-Pro

<400> SEQUENCE: 455

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 456
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isobutyloxycarbonyl-Pro

<400> SEQUENCE: 456

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 457
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Octyl-Gly

<400> SEQUENCE: 457

Gly Pro Lys Pro Glu Ala Pro Gly Glu Asp Ala Ser Pro Glu Glu Leu
1               5                   10                  15

Ala Arg Tyr Tyr Ala Ser Leu Arg Ala Tyr Ile Asn Leu Ile Thr Arg
            20                  25                  30

Gln Arg Tyr
        35

<210> SEQ ID NO 458
<211> LENGTH: 34

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 458

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Phe

<210> SEQ ID NO 459
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 459

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Trp

<210> SEQ ID NO 460
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 460

Pro Lys Pro Glu Ala Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 461
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 461

Pro Lys Pro Glu Ala Pro Gly Glu Asp Ala Ser Ala Glu Glu Leu Ala
1               5                   10                  15
```

Arg Tyr Tyr Ala Ser Leu Arg Ala Tyr Ile Asn Leu Ile Thr Arg Gln
            20                  25                  30

Arg Tyr

<210> SEQ ID NO 462
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 462

Pro Lys Pro Glu His Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 463
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 463

Pro Ser Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 464
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 464

Pro Lys Pro Glu Gly Pro Ala Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 465
<211> LENGTH: 34
<212> TYPE: PRT

<213> ORGANISM: Artificial Sequence
<220> FEATURE:
<223> OTHER INFORMATION: Description of Artificial Sequence: Synthetic
      peptide construct

<400> SEQUENCE: 465

Pro Lys Pro Glu Ala Pro Gly Glu Asp Pro Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 466
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 466

Pro Lys Pro Glu Ala Pro Gly Glu Asp Pro Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 467
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 467

Val Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 468
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Val

<400> SEQUENCE: 468

Val Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 469
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 469

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 470
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 470

Pro Lys Pro Glu His Pro Gly Glu Asp Ala Pro Ala Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 471
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 471

Pro Lys Pro Glu His Pro Gly Glu Asp Ala Pro Ser Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 472
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Pro

<400> SEQUENCE: 472

Pro Lys Pro Glu His Pro Gly Glu Asp Ala Pro Ser Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 473
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile

<400> SEQUENCE: 473

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 474
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: 8-amino octanoyl-Ile

<400> SEQUENCE: 474

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 475
<211> LENGTH: 36
<212> TYPE: PRT
<213> ORGANISM: Artificial Sequence
<220> FEATURE:
<223> OTHER INFORMATION: Description of Artificial Sequence: N-term BH
      modified

<400> SEQUENCE: 475

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 476
<211> LENGTH: 36

-continued

```
<212> TYPE: PRT
<213> ORGANISM: Artificial Sequence
<220> FEATURE:
<223> OTHER INFORMATION: Description of Artificial Sequence: N-term BH
      modified

<400> SEQUENCE: 476

Tyr Pro Ile Ala Pro Glu Ala Pro Gly Glu Asp Ala Ser Pro Glu Glu
1               5                   10                  15
Leu Ala Gln Tyr Ala Ala Asp Leu Arg Arg Tyr Ile Asn Met Leu Thr
            20                  25                  30
Arg Gln Arg Tyr
            35

<210> SEQ ID NO 477
<211> LENGTH: 34
<212> TYPE: PRT
<213> ORGANISM: Artificial Sequence
<220> FEATURE:
<223> OTHER INFORMATION: Description of Artificial Sequence: N-term BH
      modified

<400> SEQUENCE: 477

Ile Ala Pro Glu Ala Pro Gly Glu Asp Ala Ser Pro Glu Glu Leu Ala
1               5                   10                  15
Gln Tyr Ala Ala Asp Leu Arg Arg Tyr Ile Asn Met Leu Thr Arg Gln
            20                  25                  30
Arg Tyr

<210> SEQ ID NO 478
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Isocaproyl-Ile
<220> FEATURE:
<221> NAME/KEY: MOD_RES
<222> LOCATION: (2)..(2)
<223> OTHER INFORMATION: BH modified Lys

<400> SEQUENCE: 478

Ile Lys Pro Glu Ala Pro Gly Glu Asp Ala Ser Pro Glu Glu Leu Ala
1               5                   10                  15
Gln Tyr Ala Ala Asp Leu Arg Arg Tyr Ile Asn Met Leu Thr Arg Gln
            20                  25                  30
Arg Tyr

<210> SEQ ID NO 479
<211> LENGTH: 34
<212> TYPE: PRT
<213> ORGANISM: Artificial Sequence
<220> FEATURE:
<223> OTHER INFORMATION: Description of Artificial Sequence: N-term BH
      modified

<400> SEQUENCE: 479

Pro Lys Pro Glu Ala Pro Gly Glu Asp Ala Ser Pro Glu Glu Leu Ala
1               5                   10                  15
Arg Tyr Tyr Ala Ser Leu Arg Ala Tyr Ile Asn Leu Ile Thr Arg Gln
            20                  25                  30
```

Arg Tyr

```
<210> SEQ ID NO 480
<211> LENGTH: 34
<212> TYPE: PRT
<213> ORGANISM: Artificial Sequence
<220> FEATURE:
<223> OTHER INFORMATION: Description of Artificial Sequence: N-term BH
      modified

<400> SEQUENCE: 480
```

Pro Ala Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

```
<210> SEQ ID NO 481
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Tyr, or absent
<220> FEATURE:
<221> NAME/KEY: MOD_RES
<222> LOCATION: (2)..(2)
<223> OTHER INFORMATION: Ile, Pro, or absent
<220> FEATURE:
<221> NAME/KEY: MOD_RES
<222> LOCATION: (3)..(3)
<223> OTHER INFORMATION: Ile, Lys, Val, or Pro
<220> FEATURE:
<221> NAME/KEY: MOD_RES
<222> LOCATION: (4)..(4)
<223> OTHER INFORMATION: Lys, Ala, Ser, or Arg
<220> FEATURE:
<221> NAME/KEY: MOD_RES
<222> LOCATION: (7)..(7)
<223> OTHER INFORMATION: Ala, Gly, or His
<220> FEATURE:
<221> NAME/KEY: MOD_RES
<222> LOCATION: (9)..(9)
<223> OTHER INFORMATION: Gly, or Ala
<220> FEATURE:
<221> NAME/KEY: MOD_RES
<222> LOCATION: (12)..(12)
<223> OTHER INFORMATION: Ala, or Pro
<220> FEATURE:
<221> NAME/KEY: MOD_RES
<222> LOCATION: (13)..(13)
<223> OTHER INFORMATION: Ser, or Pro
<220> FEATURE:
<221> NAME/KEY: MOD_RES
<222> LOCATION: (14)..(14)
<223> OTHER INFORMATION: Pro, Ala or Ser
<220> FEATURE:
<221> NAME/KEY: MOD_RES
<222> LOCATION: (16)..(16)
<223> OTHER INFORMATION: Glu, or Asp
<220> FEATURE:
<221> NAME/KEY: MOD_RES
<222> LOCATION: (17)..(17)
<223> OTHER INFORMATION: Leu or Ile
<220> FEATURE:
<221> NAME/KEY: MOD_RES
<222> LOCATION: (18)..(18)
<223> OTHER INFORMATION: Asn, or Ala
<220> FEATURE:
```

```
<221> NAME/KEY: MOD_RES
<222> LOCATION: (19)..(19)
<223> OTHER INFORMATION: Arg, Lys, Gln, or N(Me)Ala
<220> FEATURE:
<221> NAME/KEY: MOD_RES
<222> LOCATION: (21)..(21)
<223> OTHER INFORMATION: Tyr, Ala, Phe, or Lys
<220> FEATURE:
<221> NAME/KEY: MOD_RES
<222> LOCATION: (22)..(22)
<223> OTHER INFORMATION: Ala, or Ser
<220> FEATURE:
<221> NAME/KEY: MOD_RES
<222> LOCATION: (23)..(23)
<223> OTHER INFORMATION: Ser, Ala, or Asp
<220> FEATURE:
<221> NAME/KEY: MOD_RES
<222> LOCATION: (25)..(25)
<223> OTHER INFORMATION: Arg, or Lys
<220> FEATURE:
<221> NAME/KEY: MOD_RES
<222> LOCATION: (26)..(26)
<223> OTHER INFORMATION: His, Ala, or Arg
<220> FEATURE:
<221> NAME/KEY: MOD_RES
<222> LOCATION: (28)..(28)
<223> OTHER INFORMATION: Leu, or Ile
<220> FEATURE:
<221> NAME/KEY: MOD_RES
<222> LOCATION: (30)..(30)
<223> OTHER INFORMATION: Leu, or Met
<220> FEATURE:
<221> NAME/KEY: MOD_RES
<222> LOCATION: (31)..(31)
<223> OTHER INFORMATION: Val, Ile, or Leu
<220> FEATURE:
<221> NAME/KEY: MOD_RES
<222> LOCATION: (35)..(35)
<223> OTHER INFORMATION: Lys, or Arg
<220> FEATURE:
<221> NAME/KEY: MOD_RES
<222> LOCATION: (36)..(36)
<223> OTHER INFORMATION: Tyr, Trp, or Phe

<400> SEQUENCE: 481

Xaa Xaa Xaa Xaa Pro Glu Xaa Pro Xaa Glu Asp Xaa Xaa Xaa Glu Xaa
1               5                   10                  15

Xaa Xaa Xaa Tyr Xaa Xaa Xaa Leu Xaa Xaa Tyr Xaa Asn Xaa Xaa Thr
            20                  25                  30

Arg Gln Xaa Xaa
        35

<210> SEQ ID NO 482
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Tyr, or absent
<220> FEATURE:
<221> NAME/KEY: MOD_RES
<222> LOCATION: (2)..(2)
<223> OTHER INFORMATION: Ile, Pro, or absent
<220> FEATURE:
<221> NAME/KEY: MOD_RES
<222> LOCATION: (4)..(4)
<223> OTHER INFORMATION: Lys, Ala, Ser, or Arg
<220> FEATURE:
<221> NAME/KEY: MOD_RES
<222> LOCATION: (6)..(6)
<223> OTHER INFORMATION: Glu, Gln, Ala, Asn, Asp, or Val
```

```
<220> FEATURE:
<221> NAME/KEY: MOD_RES
<222> LOCATION: (9)..(9)
<223> OTHER INFORMATION: Gly, or Ala
<220> FEATURE:
<221> NAME/KEY: MOD_RES
<222> LOCATION: (10)..(10)
<223> OTHER INFORMATION: Glu, Ala, Asp, Asn, Gln, Gly, Pro, or Aib
<220> FEATURE:
<221> NAME/KEY: MOD_RES
<222> LOCATION: (11)..(11)
<223> OTHER INFORMATION: Glu, Ala, Asp, Asn, Gln, Gly, Pro, or Aib
<220> FEATURE:
<221> NAME/KEY: MOD_RES
<222> LOCATION: (12)..(12)
<223> OTHER INFORMATION: Ala, or Pro
<220> FEATURE:
<221> NAME/KEY: MOD_RES
<222> LOCATION: (13)..(13)
<223> OTHER INFORMATION: Ser, or Pro
<220> FEATURE:
<221> NAME/KEY: MOD_RES
<222> LOCATION: (14)..(14)
<223> OTHER INFORMATION: Pro, Ala or Ser
<220> FEATURE:
<221> NAME/KEY: MOD_RES
<222> LOCATION: (15)..(15)
<223> OTHER INFORMATION: Glu, Ala, Asp, Asn, Gln, Gly, Pro, or Aib
<220> FEATURE:
<221> NAME/KEY: MOD_RES
<222> LOCATION: (16)..(16)
<223> OTHER INFORMATION: Glu, or Asp
<220> FEATURE:
<221> NAME/KEY: MOD_RES
<222> LOCATION: (17)..(17)
<223> OTHER INFORMATION: Leu or Ile
<220> FEATURE:
<221> NAME/KEY: MOD_RES
<222> LOCATION: (19)..(19)
<223> OTHER INFORMATION: Arg, Lys, Gln, or N(Me)Ala
<220> FEATURE:
<221> NAME/KEY: MOD_RES
<222> LOCATION: (21)..(21)
<223> OTHER INFORMATION: Tyr, Ala, Phe, or Lys
<220> FEATURE:
<221> NAME/KEY: MOD_RES
<222> LOCATION: (22)..(22)
<223> OTHER INFORMATION: Ala, or Ser
<220> FEATURE:
<221> NAME/KEY: MOD_RES
<222> LOCATION: (23)..(23)
<223> OTHER INFORMATION: Ser, Ala, or Asp
<220> FEATURE:
<221> NAME/KEY: MOD_RES
<222> LOCATION: (25)..(25)
<223> OTHER INFORMATION: Arg, or Lys
<220> FEATURE:
<221> NAME/KEY: MOD_RES
<222> LOCATION: (26)..(26)
<223> OTHER INFORMATION: His, Ala, or Arg
<220> FEATURE:
<221> NAME/KEY: MOD_RES
<222> LOCATION: (27)..(27)
<223> OTHER INFORMATION: Tyr, or Phe
<220> FEATURE:
<221> NAME/KEY: MOD_RES
<222> LOCATION: (28)..(28)
<223> OTHER INFORMATION: Leu, or Ile
<220> FEATURE:
<221> NAME/KEY: MOD_RES
<222> LOCATION: (29)..(29)
<223> OTHER INFORMATION: Asn, or Gln
<220> FEATURE:
<221> NAME/KEY: MOD_RES
<222> LOCATION: (30)..(30)
<223> OTHER INFORMATION: Leu, or Met
<220> FEATURE:
<221> NAME/KEY: MOD_RES
<222> LOCATION: (31)..(31)
```

```
<223> OTHER INFORMATION: Val, Ile, or Leu

<400> SEQUENCE: 482

Xaa Xaa Pro Xaa Pro Xaa His Pro Xaa Xaa Xaa Xaa Xaa Xaa Xaa Xaa
1               5                   10                  15

Xaa Ala Xaa Tyr Xaa Xaa Xaa Leu Xaa Xaa Xaa Xaa Xaa Xaa Xaa Thr
            20                  25                  30

Arg Gln Arg Tyr
        35

<210> SEQ ID NO 483
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)..(1)
<223> OTHER INFORMATION: Ile, isocap-Ile, Pro, or isocap-Pro
<220> FEATURE:
<221> NAME/KEY: MOD_RES
<222> LOCATION: (5)..(5)
<223> OTHER INFORMATION: His or Ala
<220> FEATURE:
<221> NAME/KEY: MOD_RES
<222> LOCATION: (13)..(13)
<223> OTHER INFORMATION: Ala or absent
<220> FEATURE:
<221> NAME/KEY: MOD_RES
<222> LOCATION: (21)..(21)
<223> OTHER INFORMATION: Ala or Ser
<220> FEATURE:
<221> NAME/KEY: MOD_RES
<222> LOCATION: (22)..(22)
<223> OTHER INFORMATION: Ala or Ser
<220> FEATURE:
<221> NAME/KEY: MOD_RES
<222> LOCATION: (25)..(25)
<223> OTHER INFORMATION: Ala or His

<400> SEQUENCE: 483

Xaa Lys Pro Glu Xaa Pro Gly Glu Asp Ala Ser Pro Xaa Glu Glu Leu
1               5                   10                  15

Ala Arg Tyr Tyr Xaa Xaa Leu Arg Xaa Tyr Ile Asn Leu Ile Thr Arg
            20                  25                  30

Gln Arg Tyr
        35
```